US009498476B2

(12) United States Patent
Qiu et al.

(10) Patent No.: US 9,498,476 B2
(45) Date of Patent: Nov. 22, 2016

(54) CRYSTALLINE FORM OF 6-[(4S)-2-METHYL-4-(2-NAPHTHYL)-1,2,3,4-TETRAHYDROISOQUINOLIN-7-YL]PYRIDAZIN-3-AMINE

(71) Applicants: Bristol-Myers Squibb Company, Princeton, NJ (US); Albany Molecular Research, Inc., Albany, NY (US)

(72) Inventors: Jun Qiu, Kendall Park, NJ (US); Qi Gao, Franklin Park, NJ (US); Shuang Liu, Schenectady, NY (US); Min Hu, Schenectady, NY (US); Yuh-Lin Allen Yang, Bay Point, CA (US); Matthew Isherwood, Del Mar, NY (US); Rasidul Amin, East Greenbush, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 14/841,024

(22) Filed: Aug. 31, 2015

(65) Prior Publication Data
US 2015/0366864 A1 Dec. 24, 2015

Related U.S. Application Data

(62) Division of application No. 13/845,919, filed on Mar. 18, 2013, now Pat. No. 9,156,812, which is a division of application No. 12/995,771, filed as application No. PCT/US2009/046256 on Jun. 4, 2009, now Pat. No. 8,445,494.

(60) Provisional application No. 61/058,717, filed on Jun. 4, 2008.

(51) Int. Cl.
*A61K 31/435* (2006.01)
*A61K 31/495* (2006.01)
*A61K 31/501* (2006.01)
*C07D 401/04* (2006.01)

(52) U.S. Cl.
CPC ............ *A61K 31/501* (2013.01); *A61K 31/435* (2013.01); *A61K 31/495* (2013.01); *C07D 401/04* (2013.01)

(58) Field of Classification Search
CPC . A61K 31/435; A61K 31/495; A61K 31/501
See application file for complete search history.

(56) References Cited

U.S. PATENT DOCUMENTS

| | | |
|---|---|---|
| 3,666,763 A | 5/1972 | Grethe et al. |
| 3,947,456 A | 3/1976 | Rheiner |
| 4,113,869 A | 9/1978 | Gardner |
| 4,340,600 A | 7/1982 | Brenner et al. |
| 4,564,613 A | 1/1986 | Boltze et al. |
| 4,843,071 A | 6/1989 | Hohenwarter |
| 4,902,710 A | 2/1990 | Foster et al. |
| 5,212,185 A | 5/1993 | Hanson |
| 5,241,065 A | 8/1993 | Berger et al. |
| 5,444,070 A | 8/1995 | Moldt et al. |
| 5,447,947 A | 9/1995 | Campbell |
| 5,532,244 A | 7/1996 | Wong et al. |
| 5,587,380 A | 12/1996 | Miller et al. |
| 5,595,872 A | 1/1997 | Wetterau, II |
| 5,654,296 A | 8/1997 | Kato et al. |
| 5,654,316 A | 8/1997 | Carruthers et al. |
| 5,656,642 A | 8/1997 | Fujioka et al. |
| 5,789,449 A | 8/1998 | Norden |
| 5,817,832 A | 10/1998 | Wallquist et al. |
| 5,827,875 A | 10/1998 | Dickson, Jr. et al. |
| 5,843,967 A | 12/1998 | Riedl et al. |
| 5,885,983 A | 3/1999 | Biller et al. |
| 6,043,253 A | 3/2000 | Brockunier et al. |
| 6,121,261 A | 9/2000 | Glatt et al. |
| 6,136,803 A | 10/2000 | Freedman et al. |
| 6,162,809 A | 12/2000 | Kohl et al. |
| 6,211,170 B1 | 4/2001 | Yaokim et al. |
| 6,218,404 B1 | 4/2001 | Bigge et al. |
| 6,239,125 B1 | 5/2001 | Melenfant et al. |
| 6,262,074 B1 | 7/2001 | Otten et al. |
| 6,340,681 B1 | 1/2002 | Ito |
| 6,358,993 B1 | 3/2002 | Reddy et al. |
| 6,441,244 B1 | 8/2002 | Avar et al. |
| 6,479,436 B1 | 11/2002 | Otten et al. |
| 6,506,772 B1 | 1/2003 | Brodbeck et al. |
| 6,506,773 B2 | 1/2003 | Hannah et al. |
| 6,562,836 B1 | 5/2003 | Szarek et al. |
| 6,579,885 B2 | 6/2003 | Beck et al. |
| 6,586,447 B1 | 7/2003 | Lyssikatos et al. |

(Continued)

FOREIGN PATENT DOCUMENTS

| | | |
|---|---|---|
| CA | 2015114 | 10/1990 |
| CH | 538 477 | 8/1973 |

(Continued)

OTHER PUBLICATIONS

International Preliminary Report on Patentability and Written Opinion for PCT/US2014/023938 dated Sep. 15, 2015.
Translation of Office Action for Mexican Patent Application No. MX/a/2011/011907 (Oct. 1, 2015) (redacted).
Examination Report for Australian National Patent Application No. 2010247763 (Oct. 21, 2014).
Translation of Reexamination Notice for Chinese Patent Application No. 201080031666.3 (Aug. 14, 2015).
Office Action dated Jul. 2, 2015 for U.S. Appl. No. 14/661,063.
First examination report for European National Patent Application No. 09759417.0 (Sep. 15, 2015).
International Search Report and Written Opinion for International Application PCT/US2009/046256 dated Dec. 9, 2009.
Office Action dated Dec. 19, 2014 for U.S. Appl. No. 13/664,546.
PCT International Search Report corresponding to PCT/US2014/023938, filed Mar. 12, 2014 (mailed Sep. 29, 2014).
International Search Report and Written Opinion for International Application PCT/US2009/046259 dated Mar. 1, 2010.
International Preliminary Report On Patentability for International Application PCT/US2009/046259 dated Dec. 6, 2010.

(Continued)

*Primary Examiner* — Yong Chong
(74) *Attorney, Agent, or Firm* — LeClairRyan, a Professional Corporation

(57) ABSTRACT

The present disclosure generally relates to a crystalline form of 6-[(4S)-2-methyl-4-(naphthyl)-1,2,3,4-tetrahydroisoquinolin-7-yl]pyridazin-3-amine. The present disclosure also generally relates to pharmaceutical compositions comprising the crystalline form, as well of methods of using a crystalline form in the treatment of depression and other conditions and methods for obtaining such crystalline form.

2 Claims, 3 Drawing Sheets

(56) References Cited

U.S. PATENT DOCUMENTS

| | | |
|---|---|---|
| 6,642,228 B1 | 11/2003 | Hayashi et al. |
| 6,664,256 B1 | 12/2003 | Ohkuchi et al. |
| 6,664,293 B2 | 12/2003 | Yamada et al. |
| 6,703,405 B2 | 3/2004 | Hofmeister et al. |
| 6,900,220 B2 | 5/2005 | Becker et al. |
| 6,911,453 B2 | 6/2005 | Hofmeister et al. |
| 6,919,376 B2 | 7/2005 | Llompart et al. |
| 6,943,159 B1 | 9/2005 | Gouliaev et al. |
| 6,974,803 B2 | 12/2005 | Yeadon |
| 6,977,261 B2 | 12/2005 | Bunker et al. |
| 7,041,702 B1 | 5/2006 | Durant et al. |
| 7,084,152 B2 | 8/2006 | Beck et al. |
| 7,163,949 B1 | 1/2007 | Beck et al. |
| 7,211,584 B2 | 5/2007 | Jover et al. |
| 7,211,585 B2 | 5/2007 | Jover et al. |
| 7,241,774 B2 | 7/2007 | Miller et al. |
| 7,241,775 B2 | 7/2007 | Hofmeister et al. |
| 7,256,201 B2 | 8/2007 | Barlaam et al. |
| 7,265,116 B2 | 9/2007 | Beck et al. |
| 7,268,142 B2 | 9/2007 | Allen et al. |
| 7,309,789 B2 | 12/2007 | Beck et al. |
| 7,321,064 B1 | 1/2008 | Cabaj et al. |
| 7,345,057 B2 | 3/2008 | Torrens Jover et al. |
| 7,388,019 B2 | 6/2008 | Ashton et al. |
| 7,419,985 B2 | 9/2008 | Beck et al. |
| 7,425,633 B2 | 9/2008 | Jiaang et al. |
| 7,459,460 B2 | 12/2008 | Yang et al. |
| 7,491,794 B2 | 2/2009 | Blatt et al. |
| 7,501,538 B2 | 3/2009 | Mjalli et al. |
| 7,541,357 B2 | 6/2009 | Molino et al. |
| 7,544,497 B2 | 6/2009 | Sinclair et al. |
| 7,582,803 B2 | 9/2009 | Akerman et al. |
| 7,612,090 B2 | 11/2009 | Beck et al. |
| 7,790,742 B2 | 9/2010 | Lang et al. |
| 7,846,930 B2 | 12/2010 | Keith |
| 7,872,138 B2 | 1/2011 | Villani et al. |
| 7,956,050 B2 | 6/2011 | Molino et al. |
| 7,973,057 B2 | 7/2011 | Greig et al. |
| 8,178,545 B2 | 5/2012 | Brown |
| 8,227,486 B2 | 7/2012 | Molino et al. |
| 8,236,796 B2 | 8/2012 | Molino et al. |
| 8,420,811 B2 | 4/2013 | Loben et al. |
| 8,445,494 B2 | 5/2013 | Qui et al. |
| 9,156,812 B2 | 10/2015 | Qiu et al. |
| 2003/0203920 A1 | 10/2003 | Beck et al. |
| 2004/0044000 A1 | 3/2004 | Bunker et al. |
| 2004/0248932 A1 | 12/2004 | Friail et al. |
| 2004/0248933 A1 | 12/2004 | Frail et al. |
| 2005/0020597 A1 | 1/2005 | Beck et al. |
| 2005/0113283 A1 | 5/2005 | Solow-Cordero et al. |
| 2005/0171027 A1 | 8/2005 | Sinclair et al. |
| 2005/0256318 A1 | 11/2005 | Michel |
| 2005/0261298 A1 | 11/2005 | Solow-Cordero et al. |
| 2006/0014705 A1 | 1/2006 | Howitz et al. |
| 2006/0052378 A1 | 3/2006 | Molino et al. |
| 2006/0063766 A1 | 3/2006 | Molino et al. |
| 2006/0084135 A1 | 4/2006 | Howitz et al. |
| 2006/0111385 A1 | 5/2006 | Molino et al. |
| 2006/0111386 A1 | 5/2006 | Molino et al. |
| 2006/0111393 A1 | 5/2006 | Molino et al. |
| 2006/0111394 A1 | 5/2006 | Molino et al. |
| 2006/0111395 A1 | 5/2006 | Molino et al. |
| 2006/0111396 A1 | 5/2006 | Molino et al. |
| 2006/0194837 A1 | 8/2006 | Carruthers et al. |
| 2006/0217409 A1 | 9/2006 | Beck et al. |
| 2006/0229265 A1 | 10/2006 | Milburn et al. |
| 2006/0276416 A1 | 12/2006 | Sinclair et al. |
| 2007/0015737 A1 | 1/2007 | Clark et al. |
| 2007/0048728 A1 | 3/2007 | Ratcliffe et al. |
| 2007/0060589 A1 | 3/2007 | Purandare et al. |
| 2007/0082907 A1 | 4/2007 | Canada et al. |
| 2007/0105838 A1 | 5/2007 | Best et al. |
| 2007/0112012 A1 | 5/2007 | Boehringer et al. |
| 2008/0004336 A1 | 1/2008 | Gougoutas et al. |
| 2008/0207595 A9 | 8/2008 | Molino et al. |
| 2008/0318997 A1 | 12/2008 | Beck et al. |
| 2009/0048443 A1 | 2/2009 | Molino et al. |
| 2009/0069374 A1 | 3/2009 | Skolnick et al. |
| 2009/0099158 A1 | 4/2009 | Grice et al. |
| 2009/0253906 A1 | 10/2009 | Molino et al. |
| 2010/0137278 A1 | 6/2010 | Guzzo et al. |
| 2010/0210624 A1 | 8/2010 | Liu et al. |
| 2010/0292242 A1 | 11/2010 | Liu et al. |
| 2010/0292243 A1 | 11/2010 | Liu et al. |
| 2010/0292250 A1 | 11/2010 | Wei et al. |
| 2011/0003850 A1 | 1/2011 | Vernier et al. |
| 2011/0281842 A1 | 11/2011 | Michaelides et al. |
| 2012/0046271 A1 | 2/2012 | Guzzo et al. |
| 2016/0022675 A1 | 1/2016 | Gonzalez-Bobes et al. |

FOREIGN PATENT DOCUMENTS

| | | |
|---|---|---|
| DE | 2 062 001 | 7/1971 |
| DE | 102005025625 | 12/2006 |
| EP | 0 140 070 A1 | 5/1985 |
| EP | 0 360 390 A1 | 3/1990 |
| EP | 0380223 | 8/1990 |
| EP | 0 394 989 B1 | 10/1990 |
| EP | 0 400 319 A1 | 12/1990 |
| EP | 0421436 | 4/1991 |
| EP | 0 428 434 A2 | 5/1991 |
| EP | 0 429 366 B1 | 5/1991 |
| EP | 0 430 771 B1 | 6/1991 |
| EP | 0 436 334 B1 | 7/1991 |
| EP | 0 443 132 B1 | 8/1991 |
| EP | 0 482 539 B1 | 4/1992 |
| EP | 0 498 069 B1 | 8/1992 |
| EP | 0 499 313 B1 | 8/1992 |
| EP | 0 512 901 B1 | 11/1992 |
| EP | 0 512 902 A1 | 11/1992 |
| EP | 0 514 273 A1 | 11/1992 |
| EP | 0 514 274 A1 | 11/1992 |
| EP | 0 514 275 A1 | 11/1992 |
| EP | 0 514 276 A1 | 11/1992 |
| EP | 0 515 681 A1 | 12/1992 |
| EP | 0 517 589 B1 | 12/1992 |
| EP | 0 520 555 A1 | 12/1992 |
| EP | 0 522 808 A2 | 1/1993 |
| EP | 0 528 495 A1 | 2/1993 |
| EP | 0 532 456 B1 | 3/1993 |
| EP | 0 533 280 B1 | 3/1993 |
| EP | 0 536 817 A1 | 4/1993 |
| EP | 0 545 478 A1 | 6/1993 |
| EP | 0 558 156 A2 | 9/1993 |
| EP | 0 577 394 B1 | 1/1994 |
| EP | 0 585 913 B1 | 3/1994 |
| EP | 0 599 338 A2 | 6/1994 |
| EP | 0 599 538 A1 | 6/1994 |
| EP | 0 610 793 A1 | 8/1994 |
| EP | 0 634 402 A1 | 1/1995 |
| EP | 0 686 629 A2 | 12/1995 |
| EP | 0 693 489 A1 | 1/1996 |
| EP | 0 694 535 A1 | 1/1996 |
| EP | 0694543 A1 | 1/1996 |
| EP | 0 699 674 A1 | 3/1996 |
| EP | 0 707 006 B1 | 4/1996 |
| EP | 0 708 101 B1 | 4/1996 |
| EP | 0 709 375 A2 | 5/1996 |
| EP | 0 709 376 A2 | 5/1996 |
| EP | 0 714 891 A1 | 6/1996 |
| EP | 0 723 959 A1 | 7/1996 |
| EP | 0 733 632 A1 | 9/1996 |
| EP | 0 776 893 A1 | 6/1997 |
| EP | 0 699 655 B1 | 9/1997 |
| EP | 0 520 555 B1 | 9/1999 |
| GB | 2 266 529 A | 11/1993 |
| GB | 2 268 931 A | 1/1994 |
| GB | 2 269 170 A | 2/1994 |
| GB | 2 269 590 A | 2/1994 |
| GB | 2 271 566 A | 4/1994 |
| GB | 2 271 774 A | 4/1994 |
| GB | 2 292 144 A | 2/1996 |
| GB | 2 293 168 A | 3/1996 |
| GB | 2 293 169 A | 3/1996 |

(56) References Cited

FOREIGN PATENT DOCUMENTS

| | | |
|---|---|---|
| GB | 2 302 689 A | 1/1997 |
| HU | 9903186 | 2/2000 |
| JP | 52-23083 | 2/1977 |
| JP | 02-281203 | 11/1990 |
| JP | 04193867 | 7/1992 |
| JP | 10-292008 | 11/1998 |
| JP | 200186110 | 7/2000 |
| JP | 2001026580 | 1/2001 |
| JP | 2003513074 | 4/2003 |
| JP | 2004501860 | 1/2004 |
| WO | WO 90/05525 | 5/1990 |
| WO | WO 90/05729 | 5/1990 |
| WO | WO 91/09844 | 7/1991 |
| WO | WO 91/18899 | 12/1991 |
| WO | WO 92/01688 | 2/1992 |
| WO | WO 92/06079 | 4/1992 |
| WO | WO 92/12151 | 7/1992 |
| WO | WO 92/15585 | 9/1992 |
| WO | WO 92/17449 | 10/1992 |
| WO | WO 92/20661 | 11/1992 |
| WO | WO 92/20676 | 11/1992 |
| WO | WO 92/21677 | 12/1992 |
| WO | WO 92/22569 | 12/1992 |
| WO | WO 93/00330 | 1/1993 |
| WO | WO 93/00331 | 1/1993 |
| WO | WO 93/01159 | 1/1993 |
| WO | WO 93/01165 | 1/1993 |
| WO | WO 93/01169 | 1/1993 |
| WO | WO 93/01170 | 1/1993 |
| WO | WO 93/06099 | 4/1993 |
| WO | WO 93/09116 | 5/1993 |
| WO | WO 93/10073 | 5/1993 |
| WO | WO 93/14084 | 7/1993 |
| WO | WO 93/14113 | 7/1993 |
| WO | WO 93/18023 | 9/1993 |
| WO | WO 93/19064 | 9/1993 |
| WO | WO 93/21155 | 10/1993 |
| WO | WO 93/21181 | 10/1993 |
| WO | WO 93/23380 | 11/1993 |
| WO | WO 93/24465 | 12/1993 |
| WO | WO 94/00440 | 1/1994 |
| WO | WO 94/01402 | 1/1994 |
| WO | WO 94/02461 | 2/1994 |
| WO | WO 94/02595 | 2/1994 |
| WO | WO 94/03429 | 2/1994 |
| WO | WO 94/03445 | 2/1994 |
| WO | WO 94/04494 | 3/1994 |
| WO | WO 94/04496 | 3/1994 |
| WO | WO 94/05625 | 3/1994 |
| WO | WO 94/07843 | 4/1994 |
| WO | WO 94/08997 | 4/1994 |
| WO | WO 94/10165 | 5/1994 |
| WO | WO 94/10167 | 5/1994 |
| WO | WO 94/10168 | 5/1994 |
| WO | WO 94/10170 | 5/1994 |
| WO | WO 94/11368 | 5/1994 |
| WO | WO 94/13639 | 6/1994 |
| WO | WO 94/13663 | 6/1994 |
| WO | WO 94/14767 | 7/1994 |
| WO | WO 94/15903 | 7/1994 |
| WO | WO 94/19320 | 9/1994 |
| WO | WO 94/19323 | 9/1994 |
| WO | WO 94/20500 | 9/1994 |
| WO | WO 94/26735 | 11/1994 |
| WO | WO 94/26740 | 11/1994 |
| WO | WO 94/29309 | 12/1994 |
| WO | WO 95/02595 | 1/1995 |
| WO | WO 95/04040 | 2/1995 |
| WO | WO 95/04042 | 2/1995 |
| WO | WO 95/06645 | 3/1995 |
| WO | WO 95/07886 | 3/1995 |
| WO | WO 95/07908 | 3/1995 |
| WO | WO 95/08549 | 3/1995 |
| WO | WO 95/11880 | 5/1995 |
| WO | WO 95/14017 | 5/1995 |
| WO | WO 95/15311 | 6/1995 |
| WO | WO 95/16679 | 6/1995 |
| WO | WO 95/17382 | 6/1995 |
| WO | WO 95/18124 | 7/1995 |
| WO | WO 95/18129 | 7/1995 |
| WO | WO 95/20575 | 8/1995 |
| WO | WO 95/21819 | 8/1995 |
| WO | WO 95/22525 | 8/1995 |
| WO | WO 95/23798 | 9/1995 |
| WO | WO 95/26338 | 10/1995 |
| WO | WO 95/28418 | 10/1995 |
| WO | WO 95/30674 | 11/1995 |
| WO | WO 95/30687 | 11/1995 |
| WO | WO 95/33744 | 12/1995 |
| WO | WO 96/05181 | 2/1996 |
| WO | WO 96/05193 | 2/1996 |
| WO | WO 96/05203 | 2/1996 |
| WO | WO 96/06094 | 2/1996 |
| WO | WO 96/07649 | 3/1996 |
| WO | WO 96/10562 | 4/1996 |
| WO | WO 96/16939 | 6/1996 |
| WO | WO 96/18643 | 6/1996 |
| WO | WO 96/20197 | 7/1996 |
| WO | WO 96/21661 | 7/1996 |
| WO | WO 96/29304 | 9/1996 |
| WO | WO 96/29317 | 9/1996 |
| WO | WO 96/29326 | 9/1996 |
| WO | WO 96/29328 | 9/1996 |
| WO | WO 96/31214 | 10/1996 |
| WO | WO 96/32385 | 10/1996 |
| WO | WO 96/37489 | 11/1996 |
| WO | WO 97/01553 | 1/1997 |
| WO | WO 97/01554 | 1/1997 |
| WO | WO 97/03066 | 1/1997 |
| WO | WO 97/08144 | 3/1997 |
| WO | WO 97/14671 | 4/1997 |
| WO | WO 97/17362 | 5/1997 |
| WO | WO 97/18206 | 5/1997 |
| WO | WO 97/19084 | 5/1997 |
| WO | WO 97/19942 | 6/1997 |
| WO | WO 97/21702 | 6/1997 |
| WO | WO 97/23458 | 7/1997 |
| WO | WO 97/36876 | 10/1997 |
| WO | WO 9743255 | 11/1997 |
| WO | WO 9743257 | 11/1997 |
| WO | WO 97/49710 | 12/1997 |
| WO | WO 9835939 | 8/1998 |
| WO | WO 98/40358 | 9/1998 |
| WO | WO 00/14076 | 3/2000 |
| WO | WO 01/32624 A1 | 5/2001 |
| WO | WO 01/32625 | 5/2001 |
| WO | 0151919 A2 | 7/2001 |
| WO | WO 0170728 | 9/2001 |
| WO | WO 02/04455 | 1/2002 |
| WO | WO 03/077874 | 9/2003 |
| WO | WO 2004067514 | 8/2004 |
| WO | WO 2004096774 | 11/2004 |
| WO | WO 2005035503 | 4/2005 |
| WO | WO 2005087235 | 9/2005 |
| WO | WO 2005095403 | 10/2005 |
| WO | WO 2006020049 | 2/2006 |
| WO | WO 2006020145 | 2/2006 |
| WO | WO 2006/057955 | 6/2006 |
| WO | WO 2006087309 | 8/2006 |
| WO | WO 2007038459 | 4/2007 |
| WO | WO 2007048788 | 5/2007 |
| WO | WO 2007098608 | 9/2007 |
| WO | WO 2007117982 | 10/2007 |
| WO | 2008003665 A1 | 1/2008 |
| WO | 2008005368 A2 | 1/2008 |
| WO | WO 2008024398 | 2/2008 |
| WO | WO 2008037482 | 4/2008 |
| WO | 2008058126 A2 | 5/2008 |
| WO | 2009149258 A2 | 12/2009 |
| WO | WO 2009/155565 | 12/2009 |
| WO | WO 2010/027500 | 3/2010 |
| WO | WO 2010132437 | 11/2010 |
| WO | WO 2010132442 | 11/2010 |
| WO | WO 2010132487 | 11/2010 |

(56) References Cited

FOREIGN PATENT DOCUMENTS

OTHER PUBLICATIONS

Ahn et al., "A Facile One-Pot Preparation of Organoselanyltrifluoroborates from Dihalobenzenes and Their Cross-Coupling Reaction," Org. Lett. 11(2):361-364 (2009).
Liang et al., "Antidepressant-Like Pharmacological Profile of a Novel Triple Reuptake Inhibitor, (1S,2S)-3-(Methylamino)-2-(naphthalen-2-yl)-1-phenylpropan-1-ol (PRC200-SS)," J. Pharmacology and Experimental Therapeutics 327(2):573-583 (2008).
Tran, "Efficacy and Tolerability of the Novel Triple Reuptake Inhibitor Amitifadine in the Treatment of Patients with Major Depressive Disorder: A Randomized, Double-Blind, Placebo-Controlled trial" J. Phychiatric Research 46:64-71 (2012).
Bennett et al., "Heteronuclear Decoupling in Rotating Solids," J. Chem. Phys., 103(16):6951-6958 (1995).
Bodkin et al., "Combining Serotonin Reuptake Inhibitors and Bupropion in Partial Responders to Antidepressant Monotherapy," J. Clin. Psychiatry, 58(4):137-145 (1997).
International Preliminary Report on Patentability for International Application PCT/US2009/046256 dated Dec. 6, 2010.
Chou et al., "Quantitative Analysis of Dose-Effect Relationships: The Combined Effects of Multiple Drugs or Enzyme Inhibitors," Adv. Enzyme Regul., 22:27-55 (1984).
Dunlop et al., "The Role of Dopamine in the Pathophysiology of Depression," Arch. Gen. Psychiatry, 64:327-337 (2007).
Earl et al., "Measurement of 13C Chemical Shifts in Solids," Journal of Magnetic Resonance, 48:35-54 (1982).
Garlow et al., Chapter 31: "The Neurochemistry of Depressive Disorders: Clinical Studies," Charney et al., eds. Neurobiology of Mental Illness, Second Edition, pp. 440-460, Oxford University Press, publ. (2004).
Gennaro, A.R., ed., Remington's Pharmaceutical Sciences, 18th Edition, p. 1445, Mack Publishing Company, publ. (1990).
Gennaro, A.R., ed., Remington's Pharmaceutical Sciences, 18th Edition, pp. xv-xvi, Mack Publishing Company, publ. (1990) (table of contents).
Gennaro, A.R., ed., Remington: The Science and Practice of Pharmacy, 19th Edition, pp. vii-viii, Mack Publishing Company, publ. (1995) (table of contents).
Hirschfeld et al., "Partial Response and Nonresponse to Antidepressant Therapy: Current Approaches and Treatment Options," J. Clin. Psychiatry, 63(9):826-837 (2002).
Kessler et al., "Prevalence, Severity, and Comorbidity of 12-Month DSM-IV Disorders in the National Comorbidity Survey Replication," Arch Gen. Psychiatry, 62:617-627 (2005).
Lavretsky et al., "Combined Treatment with Methylphenidate and Citalopram for Accelerated Response in the Elderly: An Open Trial," J. Clin. Psychiatry, 64(12):1410-1414 (2003).
Marshall et al., "Paroxetine/Bupropion Combination Treatment for Refractory Depression," J. Clin. Psychopharmacol., 16(1):80-81 (1996).
Metz et al., "Ramped-Amplitude Cross Polarization in Magic-Angle-Spinning NMR," Journal of Magnet Resonance, Series A, 110:219-227 (1994).
Mullin et al, "Programmed Cooling of Batch Crystalizers," Chemical Engineering Science, 26:369-377 (1971).
Papakostas et al., "A Metaanalysis of Clinical Trials Comparing Moclobemide with Selective Serotonin Reuptake Inhibitors for the Treatment of Major Depressive Disorder," Can J. Psychiatry, 51(12):783-790 (2006).
Stout et al., Chapter 3: "Symmetry Operations and Space Groups," X-ray Structure Determination: A Practical Guide, pp. 38-61, The Macmillan Company, publ. (1968).
Trivedi et al., "Medication Augmentation after the Failure of SSRIs for Depression," The New England Journal of Medicine, 354(12):1243-1252 (2006).
Üstün et al., "Global Burden of Depressive Disorders in the Year 2000," British Journal of Psychiatry, 184:386-392 (2004).
Yin et al., "Simulated PXRD Patterns in Studies of the Phase Composition and Thermal Behavior of Bulk Crystalline Solids," American Pharmaceutical Review, 6(2):80-85 (2003).
Hu et al., "Synthesis and Herbicidal Activity of 3-Arylalkylamino-6-chloropyridazines," Chinese Journal of Organic Chemistry, 26(6):808-812 (2006) (English Abstract only).
Translation of Substantive Examination dated Feb. 15, 2016 for Mexican Patent Application No. PI 20070018.
Translation of Office Action dated Feb. 16, 2015 for Mexican Patent Application No. MX/a/2011/011907 (redacted).
Byrn et al., "Solid-State Chemistry of Drugs," Second Edition, pp. ix-xvii, SSCI, Inc., publ. (1999) (table of contents).
Translation of Notice of Reasons for Rejection for Japanese Patent Application No. 2012-510930 dated Jun. 1, 2015.
Examination report for European Patent Application No. 10775398.0 (Aug. 20, 2015).
Office Action dated Jul. 2, 2014 for U.S. Appl. No. 13/664,546.
Translation of Decision on Rejection dated Jun. 3, 2015 for Chinese Patent Application No. 201410074721.7.
Completion of Final Requirements dated Jul. 9, 2015 for Philippine Application No. 1-2011-502550.
Office Action for U.S. Appl. No. 12/777,728 (Apr. 7, 2014).
Substantive Examination Report for Philippines Patent Application No. 1/2011/502550 (Apr. 10, 2015).
CAS Registry No. 944788-71-0, ACS on STN, 2 pages (Aug. 16, 2007).
Rollins "A Framework for Creating Customized Multi-Model Interfaces for XML Documents," Multimedia and Expo, (2000).
Translation of Office Action for Thailand Patent Application No. 0901002469 (Mar. 3, 2011) (redacted).
Translation of Notice of Reason for Refusal for Japanese Patent Application No. 2011-512645 (Nov. 12, 2013).
Translation of Notice of Decision of Refusal for Japanese Patent Application No. 2011-512645 (Oct. 28, 2014).
Translation of Office Action for Chinese Patent Application No. 200980130762.0 (Nov. 1, 2012).
Translation of Office Action for Chinese Patent Application No. 200980130762.0 (Sep. 18, 2013).
Translation of Office Action for Argentina Patent Application No. P090101990 (Jun. 27, 2012) (redacted).
Translation of Office Action for Argentina Patent Application No. P090101990 (Aug. 6, 2014) (redacted).
Translation of Office Action for Argentina Patent Application No. P090101990 (Dec. 30, 2014) (redacted).
Translation of Office Action for Taiwan Patent Application No. 098118594 (Jan. 17, 2014).
Translation of Office Action for Taiwan Patent Application No. 098118594 (Nov. 24, 2014).
Office Action for U.S. Appl. No. 12/995,771 (Dec. 20, 2011).
Office Action for U.S. Appl. No. 12/995,771 (May 9, 2012).
Office Action for U.S. Appl. No. 12/995,771 (Sep. 7, 2012).
Chen et al., "Triple Uptake Inhibitors: Therapeutic Potential in Depression and Beyond," Expert Opin. Investig. Drugs 16(9):1365-1377 (2007).
Raeder et al., "Obesity, Dyslipidemia, and Diabetes with Selective Serotoni Hordaland Health Study," J. Clin. Psychiatry 67(12):1974-82 (2006).
Lee et al., "A Review of SSRIs and SNRIs in Neuropathic Pain," Expert Opin. Pharmacother. 11(17):2813-25 (2010).
Mandal, A., "Antidepressants May Increase Stroke Risk in Men: Study," retrieved from http://www.news-medical.net/news/20110403/Antipressants (Apr. 3, 2011).
Brambilla et al., "GABAergic Dysfunction in Mood Disorders," Molecular Psychiatry 8:721-37 (2003).
Wikipedia, "Selective Serotonin Reuptake Inhibitor," retrieved from http://en.wikipedia.org/wiki/Ssri pp. 1-40 (Nov. 25, 2011).
Cohen, J.S., "The Underlying Cause of Suicides and Homicides with SSRI Antidepressants: Is it the Drugs, the Doctors, or the Drug Companies?," retrieved at http://medicationsense.com/articles/april_june_04/underlying_cause.html pp. 1-8 (Nov. 30, 2011).
Office Action for U.S. Appl. No. 14/737,897 (Jan. 15, 2016).
Examination report for European Application No. EP10775398.0 (Feb. 5, 2016).

(56) References Cited

OTHER PUBLICATIONS

Translation of Notice of Preliminary Rejection and Request for Consultation for Korean Patent Application No. 10-2011-7029425 (Apr. 25, 2016).
Office Action for U.S. Appl. No. 14/593,750 (Feb. 4, 2016).
Aihara et al., "Increasing 5-Lipoxygenase Inhibitory Activities by Oxidative Conversion of o-Methoxyphenols to Catechols Using a $Cu^{2+}$-Ascorbic Acid-$O_2$ System," *Chem. Pharm. Bull.* 38(3):842-844 (1990).
Banerji et al., "Studies on Single-Electron Transfer Reagents. Part IV Reaction of Nitrogen Heterocycles with Sodium Naphthalenide," *Tetrahedron* 50(30):9079-9096 (1994).
Beilstein No. 4048047 (CAS 17074-38-3, 17074-39-4), Beilstein Data, Elsevier Information Systems Gmbh, 2 pages (Mar. 19, 1991).
Beilstein No. 4102323 (CAS 53885-34-0), Beilstein Data, Elsevier Information Systems Gmbh, 3 pages (Mar. 19, 1991).
Beilstein No. 4341479 (CAS 134021-24-2), Beilstein Data, Elsevier Information Systems Gmbh, 5 pages (Jul. 20, 1992).
Beilstein No. 4494373 (CAS 82416-61-3), Beilstein Data, Elsevier Information Systems Gmbh, 3 pages (Dec. 2, 1991).
Beilstein No. 455853 (CAS 71730-66-0), Beilstein Data, Elsevier Information Systems Gmbh, 2 pages (Nov. 28, 1988).
Beilstein No. 4774688 (CAS 133160-36-8), Beilstein Data, Elsevier Information Systems Gmbh, 2 pages (Jul. 20, 1992).
Beilstein No. 4787749 (CAS 133043-12-6, 133160-34-6, 133160-35-7), Beilstein Data, Elsevier Information Systems Gmbh, 5 pages (Jul. 20, 1992).
Beilstein No. 4787750 (CAS 133043-12-6, 133160-34-6, 133160-35-7), Beilstein Data, Elsevier Information Systems Gmbh, 5 pages (Jul. 20, 1992).
Beilstein No. 4787836 (CAS 133043-20-6, 133043-31-9), Beilstein Data, Elsevier Information Systems Gmbh, 4 pages (Jul. 20, 1992).
Beilstein No. 4787837 (CAS 133043-20-6, 133043-31-9), Beilstein Data, Elsevier Information Systems Gmbh, 4 pages (Jul. 20, 1992).
Beilstein No. 4788234 (CAS 133043-19-3, 133043-30-8), Beilstein Data, Elsevier Information Systems Gmbh, 4 pages (Jul. 20, 1992).
Beilstein No. 4788235 (CAS 133043-19-3, 133043-30-8), Beilstein Data, Elsevier Information Systems Gmbh, 4 pages (Jul. 20, 1992).
Beilstein No. 4789758 (CAS 133043-21-7, 133043-22-8), Beilstein Data, Elsevier Information Systems Gmbh, 5 pages (Jul. 20, 1992).
Beilstein No. 594629 (CAS 53885-32-8), Beilstein Data, Elsevier Information Systems Gmbh, 2 pages (Nov. 28, 1988).
Berge et al., "Pharmaceutical Salts," *J. Pharm. Sci.* 66(1):1-19 (1977).
Blomberg et al., "The Barbier Reaction—A One Step Alternative for Syntheses via Organomagnesium Compounds," *Synthesis* pp. 18-30 (1977).
Bobowski & Gottlieb, "4-Substituted 1,2,3,4-tetrahydro-3,3-dimethylisoquinolines. II.," *J. Heterocyclic Chem.* 19(1):21-27 (1982).
Brown & Dyke, "1,2-Dihydroisoquinolines. II. Berbine Synthesis," *Tetrahedron* 22(8):2429-35 (1966).
Brown & Dyke, "1,2-Dihydroisoquinolines. III. Dimerization," *Tetrahedron* 22(8):2437-2443 (1966).
Bundgaard, "Means to Enhance Penetration," *Adv. Drug Delivery Rev.* 8:1-38 (1992).
Burrows et al., "Antidepressant Efficacy and Tolerability of the Selective Norepinephrine Reuptake Inhibitor Reboxetine: A Review," *J. Clin. Psychiatry* 59(Suppl. 14):4-7 (1998) (98819-76-2 Registry (Reboxetine)).
Bundgaard, *Design of Prodrugs*, Amsterdam, The Netherlands: Elsevier Science Publishers B.V. (1985) (Table of Contents only).
CAS No. 53885-23-7, ACS on STN, 1 page (Nov. 16, 1984).
CAS No. 53885-32-8, ACS on STN, 1 page (Nov. 16, 1984).
Chandrasekhar et al., "Highly Efficient Synthesis of 3-alkyl/aryl-4-aryl-1,2,3,4-tetrahydroisoquinolines from N,N-dibenzylaminols," *Tetrahedron Lett.* 43(10):1885-1888 (2002).
Cherpillod et al., "A Controlled Trial with Diclofensine, A New Psychoactive Drug, in the Treatment of Depression," *J. Int. Med. Res.* 9(5):324-329 (1981).
Cliffe et al., "(S)-N-tert-Butyl-3-(4-(2-methoxyphenyl)-piperazin-1-yl)-2-phenylpropanamide [(S)-WAY-100135]: A Selective Antagonist at Presynaptic and Postsynaptic-5-$HT_{1A}$ Receptors," *J. Med. Chem.* 36:1509-10 (1993).
Dandridge et al., "Synthesis, Resolution, Absolute Stereochemistry, and Enantioselectivity of 3', 4'-Dihydroxynomifensine," *J. Med. Chem.* 27:28-35 (1984).
Desai et al., "Relationship Between in Vivo Occupancy at the Dopamine Transporter and Behavioral Effects of Cocaine, GBR 12909 [1-{2-[Bis-(4-fluorophenyl)methoxy]ethyl}-4-(3-phenylpropyl)piperazine], and Benztropine Analogs," *J. Pharmacol. Exp. Ther.* 315(1):397-404 (2005).
Dudley et al., "The Actions of Xylamine on Central Noradrenergic Neurons," *J. Pharm. Exp. Ther.* 217(3):834-840 (1981).
Euerby et al., "Methylthio Activiating Groups in the Synthesis of Tetrahydroisoquinolines and Tetrahydro-2-benzazepines from N-Allyl- and N-Cinnamyl-benzylamines," *J. Chem. Research* pp. 40-41 (1987).
Gao et al., "Asymmetric Hetero Diels-Alder Reaction Catalyzed by Stable and Easily Prepared CAB Catalysts," *Tetrahedron* 50(4):979-988 (1994).
Georgiadis et al., "Synthesis and Complexation Properties of a Water-Soluble Optically Active Cyclophane Incorporating a 4-Naphthyl-1,2,3,4-tetrahydroisoquinoline Unit as a Chiral Spacer," *J. Org. Chem.* 56(10):3362-3369 (1991).
Greene et al., *Protective Groups in Organic Synthesis*, 2d. Ed., New York, New York: John Wiley & Sons, Inc. (1991) (Table of Contents only).
Hudlicky, "Fluorination with Diethylaminosulfur Trifluoride and Related Aminofluorosulfuranes," *Organic Reactions* 35:513-637 (1985).
Hyttel, "Pharmacological Characterization of Selective Serotonin Reuptake Inhibitors (SSRIs)," *Int. Clin. Psychopharmacol.* 9(Suppl. 1):19-26 (1994) (61869-08-7 Registry (Paroxetine); 59729-32-7 Registry (Citalopram); 79559-97-0 Registry (Sertraline); 54910-89-3 Registry (Fluoxetine); 54739-18-3 Registry (Fluvoxamine)).
Ishikura et al., "The Synthesis of 4-Substituted Isoquinoline Derivatives from Diethyl (4-Isoquinolyl) Borane," *Heterocycles* 26:1603-1610 (1987).
Jacob et al., "Dopamine Agonist Properties of N-Alkyl-4-(3,4-dihydroxyphenyl)-1,2,3,4-tetrahydroisoquinolines," *J. Med. Chem.* 24:1013-1015 (1981).
Jorgenson, "Preparation of Ketones from the Reaction of Organolithium Reagents with Carboxylic Acids," Dauben et al., eds., *Organic Reactions*, vol. 18, New York, New York: John Wiley & Sons, Inc., Chapter 1 (1970) (Table of Contents only).
Kakeya et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-Methoxyiminoacetamido]-3-Methyl-3-Cephem-4-Carboxylic Acid," *Chem. Pharm. Bull.* 32(2):692-698 (1984).
Kametani et al., "Studies on the Synthesis of Heterocyclic Compounds," *Tetrahedron* 31:235-238 (1975).
Kihara et al., "A Convenient Synthesis of 4-Substituted 1,2,3,4-Tetrahydroisoquinolin-4-OLS by a Novel Intramolecular Barbier Reaction and by an Insertion Reaction: Reaction Scope and Limitations," *Tetrahedron* 48(1):67-78 (1992).
Kihara et al., "Synthesis and Enantioselectivity of Optically Active 1- and 3-Substituted 4-Phenyl-1,2,3,4-Tetrahydroisoquinolin-4-ols and Related Compounds As Norepinephrine Potentiators," *Chem. Pharm. Bull.* 43(9):1543-1546 (1995).
Kihara et al., "Synthesis and Pharmacological Evaluation of Phenolic 2-Methyl-4-Phenyl-1,2,3,4,-Tetrahydroisoquinolin-4-ols As New Norepinephrine Potentiator," *Drug Design Dis.* 11(3):175-183 (1994).
Knabe & Herbort, "Dehydrogenation of Tertiary Amines with Aercury (II) Acetate in the Presence of EDTA. XIII. Oxidative Dimerization of 6,7-dimethoxy-2-methyl-1,1-diethyl-1,2,3,4-tetrahydroisoquinoline," *Archiv. der Pharmazie. und Berichte der Deutschen Pharmazeutischen Gesellschaft* 300(9):774-783 (1967).
Knabe & Renz, "Synthesis of 3,4'-Biisoquinolines," *Archiv. der Pharmazie.* (Weinheim, Germany) 307(8):612-622 (1974).

(56) References Cited

OTHER PUBLICATIONS

Krogsgaard-Larsen et al., eds., *A Textbook of Drug Design and Development*, Chur, Switzerland: Harwood Academic Publishers GmbH (1991) (portion of Table of Contents only).
Larock, *Comprehensive Organic Transformations: A Guide to Functional Group Preparation*, New York, New York: VCH Publishers, Inc. (1989) (Table of Contents only).
Maryanoff et al., "Pyrroloisoquinoline Antidepressants. 2. In-Depth Exploration of Structure-Activity Relationships," *J. Med. Chem.* 30(8):1433-1454 (1987).
McOmie, ed., *Protective Groups in Organic Chemistry*, London: Plenum Press (1973) (Table of Contents only).
Middlemiss et al., "Centrally Active 5-HT Receptor Agonists and Antagonists," *Neurosci. Biobehavioral Rev.* 16:75-82 (1992).
Miller et al., "An Efficient Synthesis of 4-Aryl-1,2,3,4-Tetrahydroisoquinolines," *Synthetic Com.* 24(8):1187-1193 (1994).
Mondeshka et al., "Synthesis, Antiulcer and Antidepressive Activity of 4-(4-Halophenyl)-2-Phenyl-1,2,3,4-Tetrahydroisoquinolines," *Il Farmaco* 49:475-480 (1994).
Müller, "Current St. John's Wort Research from Mode of Action to Clinical Efficacy," *Pharmacological Research* 47:101-109 (2003).
Nielsen et al., "Glycolamide Esters as Biolabile Prodrugs of Carboxylic Acid Agents: Synthesis, Stability, Bioconversion, and Physicochemical Properties," *J. Pharm. Sci.* 77(4):285-298 (1988).
Salama et al., "Antigenic Determinants Responsible for the Reactions of Drug-Dependent Antibodies with Blood Cells," *Br. J. Haematol.* 78:535-539 (1991).
Seebach et al., "Alkylation of Amino Acids without Loss of the Optical Activity: Preparation of α-Substituted Proline Derivatives. A Case of Self-Reproduction of Chirality," *J. American Chem. Soc.* 105(16):5390-5398 (1983).
Stille, "Zur pharmakologischen Prufung von Antidepressiva am Beispiel eines Dibenzodiazepins," *Arzneimittel-Forschung* 14:534-537 (1964) (English summary included on p. 537).
Sugiura & Hamada, "Studies on Nitrogen-Containing Heterocyclic Compounds. XXXV. Syntheses and Reduction of 4-Amino-2-cyano-1,3-dimethoxy-1,2,3,4-tetrahydroisoquinolines," *Yakugaku Zasshi* 99(6):556-563 (1979).
Sugiura et al., "Synthesis and Stereochemistry of 3,7-Diazatricyclo[4.2.2.2$^{2,5}$]dodeca-9,11-dienes Derived By [4+4] Cyclodimerization of 2,3-Dihydroisoquinoline Derivatives," *Chem. Pharm. Bull.* 46(12):1862-1865 (1998).
Tirelli et al., "Differential Effects of Direct and Indirect Dopamine Agonists on the Induction of Gnawing in C57Bl/6J Mice," *J. Pharm. Exp. Therapy* 273(1):7-15 (1995).
Trepanier et al., "3,4-Dihydroisocarbostyril and 1,2,3,4-Tetrahydroisoquinoline Derivatives of Ephedrine," *J. Med. Chem.* 16(4):342-347 (1973).
Uno & Okada, "A Novel Method for the Synthesis of 4-Isoquinolinols," *J. Heterocyclic Chem.* 28(2):341-346 (1991).
Venkov et al., "A New Synthesis of 1,2,3,4-Tetrahydro-2-Methyl-4-Phenylisoquinolines," *Synthesis* 253-255 (1990).
Zára-Kaczián et al., "8-Amino-4-Aryl-2Methyl-1,2,3,4-Tetrahydroisoquinlines: Reactions of the Amino Group Via the Diazonium Salts," *Acta Chimica Hungarica*, 12(4):573-584 (1989).
Office Action dated Jun. 16, 2011 for JP 2007-521686.
Office Action dated Aug. 20, 2010 for AU 2005274927.
Office Action dated Sep. 18, 2009 for CH 200580030990.2.
Supplemental Search Report dated Jul. 9, 2010 for EP 05793999.3.
Knabe et al., "Synthese von 3,4'-Biisochinolinen," *Archiv de Pharmazie* 307(8):612-622 (1974) (abstract in English).
Office Action dated Oct. 18, 2010 for IL 180349.
Office Action dated Mar. 18, 2011 for SI 200904617-8.
Office Action dated Mar. 5, 2009 for RU 2007105596.
Office Action dated Aug. 24, 2009 for RU 2007105596.
Office Action dated Apr. 10, 2008 for SI 2007001670.
Office Action dated Oct. 25, 2011 for Singapore Patent Application No. 200904617-8.
Office Action dated Dec. 16, 2011 for China Patent Application No. 200580030990.2.
Office Action dated Oct. 28, 2011 for U.S. Appl. No. 12/417,598.
International Search Report and Written Opinion for PCT/US2005/025193 (mailed Aug. 3, 2006).
Office Action dated Jan. 25, 2012 for U.S. Appl. No. 12/252,823.
Translation of Office Action for Colombia Patent Application No. 07 014.254.
Office Action dated Feb. 14, 2012 for EP 05793999.3.
Office Action dated Sep. 19, 2012 for EP 05793999.3.
Office Action dated Jul. 27, 2012 for India Patent Application No. 660/CHENP/2007.
Translation of Office Action dated Jun. 21, 2012 for Korea Patent Application No. 10-2007-7003549.
Translation of Office Action dated Jul. 27, 2012 for China Patent Application No. 200580030990.2.
European Search Report dated Nov. 2, 2012, for EP Application Serial No. 10775394.9.
European Search Report dated Dec. 7, 2012, for EP Application Serial No. 10775398.0.
European Search Report dated Jan. 2, 2013, for EP Application Serial No. 10775425.1.
Office Action dated Jan. 4, 2013 for China Patent Application No. 200580030990.2.
Substantive Examination Report and Search Report dated Apr. 15, 2011 for Malaysian Patent Application No. PI 20070018.
Opposition dated Jan. 22, 2013 for Chilean Patent Application No. 2810-2011 (redacted).
Office Action dated Nov. 13, 2012, for U.S. Appl. No. 12/777,840.
Office Action dated Nov. 9, 2012, for U.S. Appl. No. 12/777,776.
Search Report and Written Opinion dated Jan. 11, 2013, for Singapore Patent Application Serial No. 201108011-6.
Mondeshka et al., "Resolution, Absolute Sterochemistry and Enantiospecificity of 4-(4-bromophenyl)-2-methyl-1,2,3,4-tetrahydroisoquinoline. The Crystal and Molecular Structures of the Racemic and 4R-Enantiomeric Hydrochloride Salt Forms," *Acta. Chemica. Scandinavica* 48:689-698 (1994).
West, Solid State Chemistry and its Applications, Wiley, New York, pp. 358-365 (1988).
International Search Report and Written Opinion for International Application No. PCT/US10/34373 dated on Jun. 18, 2010.
International Search Report and Written Opinion for International Application No. PCT/US10/34379 dated on Jun. 21, 2010.
International Search Report and Written Opinion for International Application No. PCT/US10/34428 dated on Jun. 21, 2010.
Office Action dated May 31, 2012 for U.S. Appl. No. 12/777,728.
Office Action dated Mar. 5, 2013 for China Patent Application No. 201080031666.3.
Office Action dated Mar. 26, 2013 for Canadian Patent Application No. 2,573,271.
Translation of Office Action for Korean Patent Application No. 10-2013-7001614 (May 16, 2013).
Examination Report for European Patent Application No. 05793999.3 (Apr. 15, 2013).
Examination Report for New Zealand Patent Application No. 596104 (Sep. 13, 2012).
Translation of Office Action for Chinese Patent Application No. 201080031616.5 (May 2, 2013).
Translation of Office Action for Chinese Patent Application No. 200580030990.2 (Jul. 1, 2013).
Hearing Notice in Reference of India Patent Application No. 660/CHENP/2007 dated Jul. 9, 2013.
Translation of Office Action for Eurasian Patent Application No. 201171393 (Mar. 20, 2013).
Office Action dated Jun. 5, 2013 for China Patent Application No. 201080031617.X.
Translation of Office Action for Thai Patent Application No. 1101003072 (Sep. 18, 2013)(redacted).
Translation of Office Action for Mexico Patent Application No. MX/a/2011/011900 (Sep. 17, 2013)(redacted).
Examination report for European Patent Application No. 10775398.0 (Aug. 13, 2013).
Office Action dated Aug. 29, 2013 for Korean Patent Application No. 10-2007-7003549(redacted).

(56) References Cited

OTHER PUBLICATIONS

Translation of Official Action for Mexican Patent Application No. MX/a/2009/012414 (Oct. 16, 2013)(redacted).
Translation of Notice of Reasons for Rejection for Japanese Patent Application No. 2012-086151 (Oct. 11, 2013).
Written Opinion for Singapore Application No. 201108011-6 (mailed Aug. 9, 2013).
Translation of Official Action for Mexican Patent Application No. MX/a/2011/011901 (Sep. 19, 2013)(redacted).
Examination report for European Patent Application No. 05793999.3 (Oct. 16, 2013).
Examination report for Philippines Patent Application No. 1/2010/501539 (Oct. 8, 2013) (redacted).
Office Action dated Jun. 23, 2008 for U.S. Appl. No. 11/183,066.
Translation of Office Action dated Oct. 23, 2013 for Eurasian Patent Application No. 201171393 (redacted).
Translation of Office Action for Chinese Patent Application No. 201080031666.3 (Jan. 15, 2014).
Translation of Office Action for Mexican patent Application No. MX/a/2009/012414 (Feb. 5, 2014)(redacted).
Office Action dated Feb. 24, 2015 for U.S. Appl. No. 14/466,009.
Translation of Decision on Rejection for Chinese Patent Application No. 201080031666.3 (redacted).
Patent Examination Report dated Sep. 24, 2014 for Australian Application No. 2010247849.
Translation of Office Action for Chinese Patent Application No. 201080031616.5 (Sep. 29, 2014).
Examination report for European Patent Application No. 10775398.0 (Sep. 23, 2014).
Examination Report for Singapore Patent Application Serial No. 2011080116 (Sep. 16, 2014).
Translation of Notice of Reasons for Rejection for Japanese Patent Application No. 2012-510930 dated Jun. 25, 2014.
Translation of Office Action for Chinese Patent Application No. 201080031617.X dated Apr. 24, 2014.
Translation of Notice of Reasons for Rejection for Japanese Patent Application No. 2012-510933 dated Jun. 25, 2014.
Office Action for Peruvian Patent Application No. 1937-2011 dated May 15, 2014.
Translation of Office Action dated Mar. 31, 2014 for Chile Patent Application No. 2810-2011 (redacted).
Examination report for Australia Patent Application No. 2010247735 dated Jun. 6, 2014.
Translation of Notice of Reason for Rejection for Japanese Patent Application No. 2012-510952 dated Jul. 7, 2014.
Office Action dated Mar. 25, 2014 for Canadian Patent Application No. 2,573,271.
Translation of Notice of Defects dated Apr. 2, 2014 for Israel Patent Application No. 216049 (redacted).
Translation of Office Action dated Mar. 18, 2014 for Mexican Patent Application No. MX/a/2011/011900 (redacted).
Translation of Office Action dated Mar. 12, 2014 for Taiwan Patent Application No. 099115160.
Translation of Office Action dated Mar. 11, 2014 for China Patent Application No. 201080031616.5.
Translation of Office Action for Mexican Patent Application No. MX/a/2011/011907 (Aug. 12, 2014)(redacted).
Banker et al., "Modern Pharmaceutics," 3rd Ed., p. 451, 596 (1996).
Vippagunta et al., "Crystalline Solids," Adv. Drug Del. Rev. 48:3-26 (2001).
Wolff, M.E., "Burger's Medicinal Chemistry and Drug Discovery," 5th Ed., pp. 975-977 (1997).
Office Action dated Sep. 17, 2013 for U.S. Appl. No. 13/540,446.

CRYSTALLINE FORM OF 6-[(4S)-2-METHYL-4-(2-NAPHTHYL)-1,2,3,4-TETRAHYDROISOQUINOLIN-7-YL]PYRIDAZIN-3-AMINE

CROSS REFERENCE TO RELATED APPLICATIONS

This divisional application claims the benefit of U.S. Ser. No. 13/845,919 filed Mar. 18, 2013, now allowed, which is a divisional application which claims the benefit of U.S. Ser. No. 12/995,771 filed Dec. 2, 2010, now U.S. Pat. No. 8,445,494, which is the 371 National Stage of International Application No. PCT/US2009/046256 filed Jun. 4, 2009 which claims the benefit under 35 U.S.C. §119(e) of 61/058,717 filed Jun. 4, 2008, which are herein incorporated by reference in their entirety.

The present disclosure generally relates to a crystalline form of 6-[(4S)-2-methyl-4-(naphthyl)-1,2,3,4-tetrahydroisoquinolin-7-yl]pyridazin-3-amine. The present disclosure also generally relates to a pharmaceutical composition comprising a crystalline form, as well of methods of using a crystalline form in the treatment of depression and other conditions and methods for obtaining such crystalline form.

Major depression (unipolar depression) is a condition of high prevalence and very high global burden. The prevalence of the disease in the US was estimated at over 6% in a twelve month period and 16% over a lifetime (See, Kessler R. C. et al., "Prevalence, severity, and comorbidity of 12-month DSM-IV disorders in the National Comorbidity Survey Replication", *Arch. Gen. Psychiatry*, 62:617-627 (2005)). According to the World Health Organization, the impact of the disorder is high with depression being the fourth leading cause of disease burden (See, Ustun, J. L. et al., "Global burden of depressive disorders in the year 2000", *Brit. J.* Psychiatry, 184:386-392 (2004)). There are many symptoms associated with major depression. These symptoms generally fall into the two major categories of depressed mood and loss of interest and pleasure (anhedonia).

While the etiological basis of mood disorders is not clear, there are lines of evidence that indicate that the disorders are associated with a heterogeneous dysregulation of monoaminergic systems, i.e., those involving dopamine, norepinephrine and serotonin (See, Garlow, S. J. et al., "The neurochemistry of depressive disorders: clinical studies", *Neurobiology of Mental Illness,* 2nd Ed., Charney, D. S. et al., eds., pp. 440-460 (2004)). For instance, abnormalities in levels of serotonin, norepinephrine and dopamine metabolites are commonly reported in depressed patients. Furthermore, the leading pharmacotherapies applied to depression are aimed at monoamine systems, primarily serotonin and norepinephrine.

The response rate of typical antidepressants is reported to be on the order of 65% while remission from the disorder is only about 30% (See, Hirschfeld, R. M. et al., "Partial response and nonresponse to antidepressant therapy: current approaches and treatment options", *J. Clin. Psychiatry*, 63:826-837 (2002)). The onset of action of drugs for depression is often long, on the order of 4 weeks to response. Accordingly, new drugs for treating depression, as well as other conditions, that improved response rate, remission or onset would represent an important improvement over current therapies. The spectrum of symptom relief is also an important component to efficacy since selective serotonin reuptake inhibitors (SSRIs) and serotonin-norepinephrine reuptake inhibitors (SNRIs), while effective on symptoms related to depressed mood, are typically not optimally effective in the areas of motivation and interest in pleasure.

Accordingly, there is a need for increased efficacy over SSRIs and SNRIs. In addition, reduction in the degree of side effects is also desired. For example, addressing decreased libido as well as sleep and gastrointestinal disorders (GI) disorders associated with current anti-depressants would provide substantial benefits to patients.

One strategy that has emerged in antidepressant development is the use of triple reuptake inhibitors (TRUIs), which jointly inhibit reuptake of serotonin, norepinephrine, and dopamine. These compounds have been hypothesized to have a more rapid onset of activity and better efficacy over single or dual reuptake inhibitor antidepressants in part due to the addition of the dopamine component. While the monoamine theory of depression is centered around norepinephrine and serotonin, there are data that suggest the involvement of dopamine as well (See, Dunlop, B. W. et al., "The role of dopamine in the pathophysiology of depression", *Arch. Gen.* Psychiatry, 64:327-337 (2007) and Papakostas, G. I. et al., "A metaanalysis of clinical trials comparing moclobemide with selective serotonin reuptake inhibitors for the treatment of major depressive disorder", *Can. J. Psychiatry*, 51:783-790 (2006)) Motivation, concentration and the ability to experience pleasure are regulated in part through central dopaminergic systems and they are also negatively impacted in depression. Subgroups of depressed patients have also been observed to have decreased cerebrospinal fluid (csf) levels of the dopamine metabolite homovanillic acid, suggesting decreased dopaminergic function in those patients. Over the past several years, a number of studies have demonstrated the benefit of combining drugs that have dopamine transporter (DAT) inhibition properties, like bupropion and methylphenidate, with SSRIs or SNRIs (See, Marshall, R. D. et al., "Paroxetine/bupropion combination treatment for refractory depression", 16:80-81 (1996); Bodkin, J. A. et al., "Combining serotonin reuptake inhibitors and buproprion in partial responders to antidepressant monotherapy", *J. Clin. Psychiatry*, 58:137-145 (1997); Lavretsky, H. et al., "Combined treatment with methylphenidate and citalopram for accelerated response in the elderly: an open trial", *J. Clin. Psychiatry*, 64:1410-1414 (2003); Trivedi, M. H. et al., "Medication augmentation after the failure of SSRIs for depression", *N Engl. J. Med.*, 354:1243-1252 (2006)).

It is desired to provide drugs that target the DAT, serotonin transporter (SERT), and norepinephrine transporter (NET). Desirably, the drug would provide an optimal ratio of SERT, DAT and NET inhibition. Accordingly, SERT, DAT and NET occupancies are important pharmacological criteria for consideration. In one aspect of the invention, compounds are provided that lead to about 20-60% DAT occupancy while maintaining SERT occupancy greater than about 80%.

In accordance with the present disclosure, a particular crystalline form of 6-[(4S)-2-methyl-4-(naphthyl)-1,2,3,4-tetrahydroisoquinolin-7-yl]pyridazin-3-amine is provided that may be useful in treating depression in addition to a variety of other conditions, e.g., anxiety disorders, pain, attention deficit disorder (ADD), smoking cessation and obesity.

For purposes of clarification, the free base racemate of rac-6-[(4)-2-methyl-4-(naphthyl)-1,2,3,4-tetrahydroisoquinolin-7-yl]pyridazin-3-amine, represented by Formula (I) is referred to herein as Compound (1). The (4S)-enantiomer of Compound 1, represented by Formula (II), is referred to herein, in general (without reference to any specific crystalline form), as Compound 2. The crystalline form of Compound 2 in accordance with the present disclosure, also represented by Formula (II), is referred to herein as Form N-1.

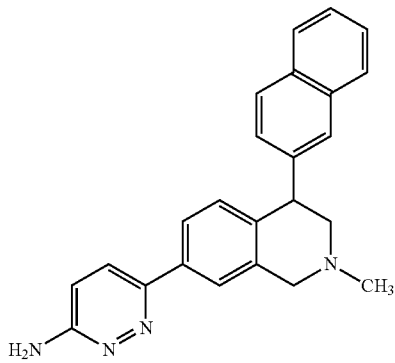

Represents Compound (1) - Racemate

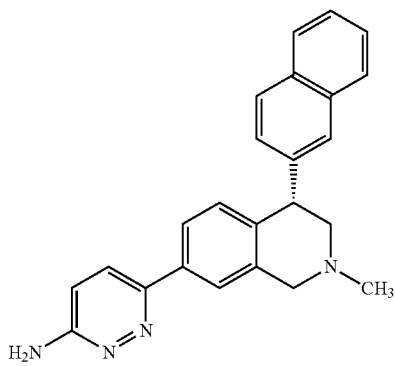

Represents Compound 2,
(4S)-enantiomer of Compound I and Form N-1

It has been found that Form N-1, can be repeatedly crystallized and provide high aqueous solubility and excellent purification capacity, thereby making it a suitable candidate for drug development.

In its first aspect, the present disclosure provides Form N-1.

In a second aspect, the present disclosure provides Form N-1, characterized by the following unit cell parameters:
Cell Dimensions:
 a=8.4299(4) Å
 b=6.0698(3) Å
 c=19.0689(12) Å
 alpha=90°
 beta=100.169(2)°
 gamma=90°
 Space group Monoclinic, P2$_1$
 Volume 960.39(9) Å$^3$
 Z, Calculated density 2, 1.267 g/cm$^3$
wherein measurement of free base crystalline form is at a temperature between about 20° C. to about 25° C.

In a third aspect, the present disclosure provides Form N-1, characterized by fractional atomic coordinates within the unit cell as listed in Table 3, Atomic Coordinates.

In a fourth aspect, the present disclosure provides Form N-1 with characteristic peaks in the powder X-ray diffraction pattern at values of two theta of 4.6±0.1, 9.4±0.1, 10.6±0.1, 14.1±0.1, 15.4±0.1, 18.2±0.1, 19.5±0.1 at a temperature between about 20° C. and about 25° C., based on a high quality pattern collected with a diffractometer (CuKα) with a spinning capillary with 2θ calibrated with a National Institute of Standards and Technology (NIST) or other suitable standard.

In a fifth aspect, the present disclosure provides Form N-1 characterized by a melt with decomposition endotherm with onset typically in the range of 235-245° C.

In a sixth aspect, the present disclosure provides substantially pure Form N-1.

In a seventh aspect, the present disclosure provides pharmaceutical compositions comprising Form N-1 and a pharmaceutically acceptable carrier or diluent.

In an eighth aspect, the present disclosure provides pharmaceutical compositions comprising Form N-1 in combination with one or more additional compounds having anti-depression activity.

Other aspects of the present disclosure may comprise suitable combinations of two or more of embodiments and/or aspects disclosed herein.

Further, other aspects of the disclosure will be apparent according to the description provided below.

DEFINITIONS

Figure 1:
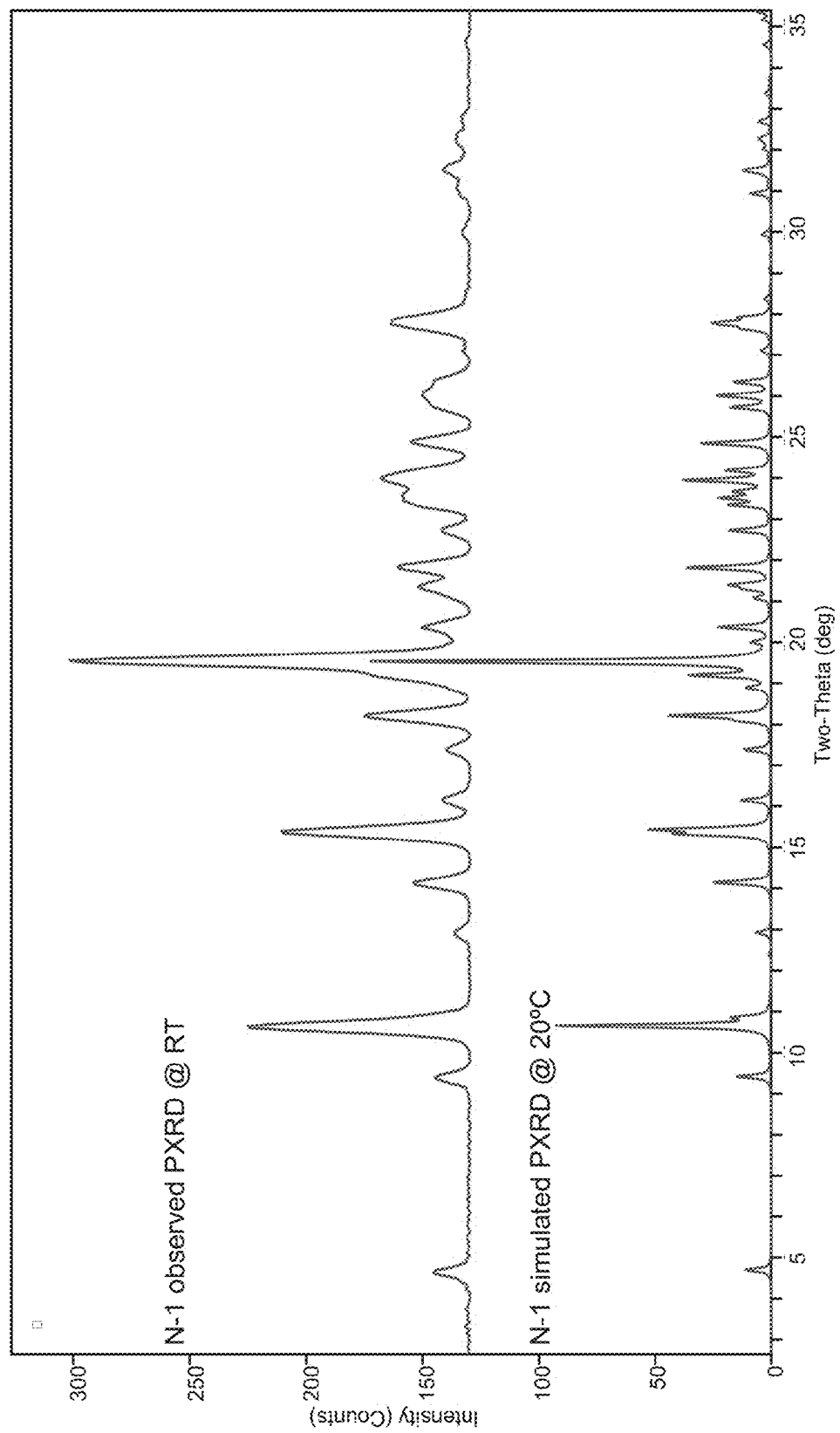
FIG. 1 illustrates experimental and simulated powdered X-ray diffraction patterns (CuKα λ=1.54178 Å at T=room temperature) of Form N-1.

Stereochemical definitions and conventions used herein generally follow *McGraw-Hill Dictionary of Chemical Terms*, Parker, S. P., ed., McGraw-Hill Book Company, New York (1984) and Eliel, E. et al., *Stereochemistry of Organic Compounds*, John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture.

The term "chiral" refers to molecules which have the property of non-superimposability of the mirror image partner, while the term "achiral" refers to molecules which are superimposable on their mirror image partner.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "enantiomers" refers to two stereoisomers of a compound which are non-superimposable mirror images of one another.

The term "halogen" as used herein and in the claims is intended to include fluorine, bromine, chlorine and iodine while the term "halide" is intended to include fluoride, bromide, chloride and iodide anion.

The term "patient" includes both human and other mammals.

The term "pharmaceutical composition" means a composition comprising Form N-1 in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18th Ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable risk/benefit ratio.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Ed., Mack Publishing Company, Easton, Pa., p. 1445 (1990). Suitable inorganic bases such as alkali and alkaline earth metal bases include The term "polymorph" refers to crystalline forms having the same chemical composition but different spatial arrangements of the molecules, atoms, and/or ions forming the crystal.

The terms "racemic mixture" and "racemate" refer to an equimolar mixture of two enantiomeric species, devoid of optical activity. In addition, as used herein, the terms "racemic mixture" and "racemate" are intended to include equimolar mixtures of two enantiomers.

The term "solvate" means a physical association of a compound of this disclosure with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "stereoisomers" refers to compounds which have identical chemical constitution, but differ with regard to the arrangement of the atoms or groups in space.

The term "substantially pure" refers to chemical purity and form purity. More specifically, substantially pure Form N-1 comprises at least about 95 wt %, preferably at least about 98 wt %, more preferably at least about 99 wt % of Form N-1 and less than about 5 wt %, preferably less than about 2 wt %, and more preferably less than about 1 wt % of other compounds having a different chemical structure than Compound 2. Additionally, substantially pure Form N-1 comprises at least about 95 wt %, preferably at least about 98 wt %, more preferably at least about 99 wt % of Form N-1 and less than about 5 wt %, preferably less than about 2 wt %, and more preferably less than about 1 wt % of any other crystalline form of Compound 2. This means that the Form N-1 preferably contains less than about 5 wt % of other compounds, and less than about 5 wt % of any other form (also referred to as "phase homogenicity").

The term "therapeutically effective amount" means the total amount of Form N-1 that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially or simultaneously. If Form N-1 is used in combination with another medication, i.e., drug, the combination of compounds described herein may result in a synergistic combination. Synergy, as described for example by Chou et al., *Adv. Enzyme Regul.,* 22:27-55 (1984), occurs when the effect of the compounds when administered in combination is greater than the effect of the compounds when administered alone as single agents.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

General Preparation of Crystalline Materials

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs. Crystals of drugs, including polymorphs, methods of preparation, and characterization of drug crystals are discussed in Byrn, S. R. et al., *Solid-State Chemistry of Drugs,* 2nd Ed., SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent, or the ability to afford a substantially pure crystalline form. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote complete or partial dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product and/or afford a substantially pure crystalline form. Accordingly, calculation of the amount of seeds needed depends on the size of the seed available and the desired size of an average product particle as described, for example, in Mullin, J. W. et al., "Programmed Cooling of Batch Crystallizers," *Chemical Engineering Science,* 26:369-377 (1971). In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity of the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, X-ray powder diffraction, or the like, to assure formation of the preferred crystalline form of the product. The resulting crystalline form is typically produced in an amount of greater than about 70 weight percent isolated yield, preferably greater than 90 weight percent isolated yield, based on the weight of the compound originally employed in the crystallization procedure. The product may be co-milled or passed through a mesh screen to delump the product, if necessary.

Crystalline forms may be prepared, for example, directly from the reaction medium of the process for preparing Compound 2. This may be achieved, for example, by employing in the final process step a solvent or a mixture of solvents from which Form N-1 may be crystallized. Alternatively, crystalline forms may be obtained by distillation or solvent addition techniques. Suitable solvents for this purpose include, for example, non-polar solvents and polar solvents, including protic polar solvents such as alcohols, and aprotic polar solvents such as ketones, the details and selection of which are known to those skilled in the art.

The presence of more than one polymorph in a sample may be determined by techniques such as powder X-ray diffraction (PXRD) or solid state nuclear magnetic resonance spectroscopy (SSNMR). For example, the presence of extra peaks in an experimentally measured PXRD pattern when compared with a simulated PXRD pattern may indicate more than one polymorph in the sample. The simulated PXRD may be calculated from single crystal X-ray data. See Smith, D. K., *A FORTRAN Program for Calculating X-ray Powder Diffraction Patterns,* Lawrence Radiation Laboratory, Livermore, Calif., UCRL-7196 (April 1963). In one aspect, Form N-1 has phase homogeneity indicated by less than 5 percent, preferably less than 2 percent, and more preferably less than 1 percent of the total peak area in the experimentally measured PXRD pattern arising from the extra peaks that are absent from a simulated PXRD pattern.

Preferably, the crystallization technique provides a product consisting essentially of Form N-1. The crystallized material preferably comprises at least 95 wt % of Form N-1, based on the weight of Compound 2 in the composition. The remaining material may comprise other form(s) of the compound and/or reaction impurities and/or processing impurities arising from its preparation. The presence of reaction impurities and/or processing impurities may be determined by analytical techniques known in the art, such as, for example, chromatography, nuclear magnetic resonance spectroscopy, mass spectrometry, or infrared spectroscopy.

Characterization

Form N-1 can be characterized using various techniques, which are well known to those of ordinary skill in the art. Examples of characterization methods include, but are not limited to, single crystal X-ray diffraction, powder X-ray diffraction (PXRD), simulated powder X-ray patterns (Yin, S. et al., *Am. Pharm. Rev.,* 6(2):80 (2003)), differential scanning calorimetry (DSC), solid-state $^{13}$C NMR (Earl, W. L. et al., *J. Magn. Reson.,* 48:35-54 (1982)), Raman spectroscopy, infrared spectroscopy, moisture sorption isotherms, thermal gravimetric analysis (TGA), and hot stage techniques.

The forms may be characterized and distinguished using single crystal X-ray diffraction, which is based on unit cell measurements of a single crystal of form N-1. A detailed description of unit cells is provided in Stout et al., Ch. 3, X-ray Structure Determination: A Practical Guide, Macmillan Co., New York (1968), which is herein incorporated by reference. Alternatively, the unique arrangement of atoms in spatial relation within the crystalline lattice may be characterized according to the observed fractional atomic coordinates. Another means of characterizing the crystalline structure is by powder X-ray diffraction analysis in which the diffraction profile is compared to a simulated profile representing pure powder material, both run at the same analytical temperature, and measurements for the subject form characterized as a series of 2θ values.

One of ordinary skill in the art will appreciate that an X-ray diffraction pattern may be obtained with a measurement of error that is dependent upon the measurement conditions employed. In particular, it is generally known that intensities in an X-ray diffraction pattern may fluctuate depending upon measurement conditions employed. It should be further understood that relative intensities may also vary depending upon experimental conditions, and, accordingly, the exact order of intensity should not be taken into account. Additionally, a measurement error of diffraction angle for a conventional X-ray diffraction pattern is typically about 5 percent or less, and such degree of measurement error should be taken into account as pertaining to the aforementioned diffraction angles. Consequently, it is to be understood that the crystal forms of the present disclosure are not limited to the crystal forms that provide X-ray diffraction patterns completely identical to the X-ray diffraction patterns depicted in the accompanying Figures disclosed herein. Any crystal form that provides an X-ray diffraction pattern, and DSC thermogram substantially identical to those disclosed in the accompanying Figures fall within the scope of the present disclosure. The ability to ascertain substantial identities of X-ray diffraction patterns is within the purview of one of ordinary skill in the art.

Utility

Form N-1, alone or in combination with other compounds, can be used to treat depression. Form N-1, alone or in combination with other compounds, can be used to treat other conditions, such as, for example, neurological conditions, psychiatric conditions and immunological conditions, e.g., anxiety disorders, pain, ADD, smoking cessation and obesity. Form N-1, alone or in combination with other compounds, i.e., drugs, can be used to treat patients afflicted with various conditions (also referred to as "disorders") by administering to said patients a dose of a pharmaceutical composition provided herein. Examples of disorders that may be treatable by pharmaceutical compositions comprising Form N-1 include, without limitation, ADD, attention deficit disorder hyperactivity disorder (ADHD), cognition impairment, anxiety disorders, especially generalized anxiety disorder (GAD), panic disorder, unipolar depression, also known as major depression, bipolar disorder, also known as manic depression or manic-depressive disorder, obsessive compulsive disorder (OCD), posttraumatic stress disorder (PTSD), acute stress disorder, social phobia, simple phobia, pre-menstrual dysphoric disorder (PMDD), social anxiety disorder (SAD), major depressive disorder (MDD), supranuclear palsy, eating disorders, especially obesity, anorexia nervosa, bulimia nervosa, and binge eating disorder, analgesia (including neuropathic pain, especially diabetic neuropathy), substance abuse disorders (including chemical dependencies) like nicotine addiction, cocaine addiction, alcohol and amphetamine addiction, Lesch-Nyhan syndrome, neurodegenerative diseases like Parkinson's disease, late luteal phase syndrome or narcolepsy, psychiatric symptoms anger such as, rejection sensitivity, movement disorders, like extrapyramidal syndrome, Tic disorders and restless leg syndrome (RLS), tardive dyskinesia, supranuclear palsy, sleep related eating disorder (SRED), night eating syndrome (NES), urinary incontinence (including stress urinary incontinence (SUI) and mixed incontinence), migraine, fibromyalgia syndrome (FS), chronic fatigue syndrome (CFS), sexual dysfunction especially premature ejaculation and male impotence, thermoregulatory disorders (e.g., hot flashes that may be associated with menopause), and lower back pain.

The present disclosure also provides pharmaceutical compositions comprising a therapeutically effective amount of Form N-1 and at least one pharmaceutically acceptable carrier.

The active ingredient, i.e., Form N-1 in such compositions typically comprises from 0.1 weight percent to 99.9 percent by weight of the composition, and often comprises from about 5 to 95 weight percent. In some cases, the pH of the formulation may be adjusted with pharmaceutically acceptable modifiers (such as calcium carbonate and magnesium oxide) to enhance the stability of the formulated compound or its delivery form. Formulations of the polymorph of the present disclosure may also contain additives for enhancement of absorption and bioavailability, or to improve the formulation process.

The pharmaceutical compositions of this disclosure may be administered orally (as a solution or solid formulation), parenterally or via an implanted reservoir. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents and suspending agents. The details concerning the preparation of such compounds are known to those skilled in the art.

When orally administered, the pharmaceutical compositions of this disclosure may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, can also be added. For oral administration in a capsule form, useful carriers/diluents include lactose, high and low molecular weight polyethylene glycol, and dried corn starch. When aqueous suspensions are administered orally, the active ingredient is combined with emulsifying and suspending agents. If desired, certain sweetening and/or flavoring and/or coloring agents may be added.

Other suitable carriers for the above noted compositions can be found in standard pharmaceutical texts, e.g., in *Remington's Pharmaceutical Sciences,* 19th Ed., Mack Publishing Company, Easton, Pa. (1995). Further details concerning the design and preparation of suitable delivery forms of the pharmaceutical compositions of the disclosure are known to those skilled in the art.

As the skilled artisan will appreciate, the appropriate dosage of Form N-1 may be determined by a skilled medical practitioner. Specific dosage and treatment regimens for any particular patient will depend upon a variety of factors, including the activity of the specific compound employed, the age, body weight, general health status, gender, diet, time of administration, the duration of treatment, rate of excretion, drug combination, the severity and course of the condition, the patient's disposition to the condition and the judgment of the treating physician.

The following non-limiting examples of reaction schemes that can be used to prepare Form N-1. Synthesis schemes are illustrated below.

Preparation of Compound 2

Synthesis of compound 2 utilizes a general approach for C-7 and C-4 substituted tetrahydroisoquinolines. A functional handle at C-7, allows the installation of the heterocycle using a palladium-catalyzed Suzuki coupling and the aryl substituent at C-4 is incorporated from commercially available starting materials. Although the route was racemic, the first synthesis relied on separation of the racemic drug substance using in preparative chiral chromatography. The second generation route relied on a classical resolution of an appropriate intermediate using di-p-toluoyl-D-tartaric acid (Synthesis Scheme 1).

The preferred synthesis begins with the reductive amination of commercially available m-anisealdehyde using methyl amine and sodium bororhydride in an appropriate solvent such as a mixture of methanol and water to afford compound 3 in quantitative yield (Synthesis Scheme 1). In this example the methoxy group will be the functional handle for installation of the C-7 pyridazine heterocycle. Alternatively m-bromobenzaldehyde has been demonstrated to be a suitable starting material (Synthesis Scheme 2). A number of alternative reducing agents can be envisioned to install the amine functionality Alkylation of the secondary amine with α-bromo-2'-acetonapthone and an appropriate base composed of either an organic amine bases such as triethylamine, afforded ketone compound 4. Dichloromethane is the preferred solvent, although a number of solvents can be used including EtOAc, IPAC, MTBE, MeOH, EtOH, THF, ACN Immediate reduction of the resulting ketone with sodium borohydride afforded compound 5 which was subsequently cyclized under acidic Friedel-Crafts conditions to afford racemic tetrahydroisoquinoline compound 6 and its regioisomer in approximately 2.5:1 ratio. A number of acids can be envisioned including protic acids such as methanesulfonic acid and sulfuric acid and Lewis acids such as TiCl$_4$ and AlCl$_3$. The regioisomers are separated via the oxlate salts and then a selective crystallization in ethanol. The oxalate salt of the desired isomer is then converted to the free base by treatment with aqueous sodium hydroxide and subsequently isolated by extraction with MTBE. A second iteration of this procedure improves the ration to >97:3. Classical resolution of the desired enantiomer, compound 7, is achieved using di-p-toluoyl-D-tartaric acid. The desired tartrate salt is more insoluble in acetone, and isolated by filtration. After treatment with aqueous sodium hydroxide to afford the free base, the first pass affords a 95:5 mixture of enantiomers. A second iteration provides >99% ee with chemical purity >99%. Alternatively the mixture of stereo- and regioisomers could be purified by chiral SFC chromatography. Demethylation of compound 7 with hydrobromic acid in acetic acid affords the phenol hydrobromide salt, compound 8, which is converted directly to the triflate, compound 9, by using two equivalents of an organic amine base, such as triethyl amine, DIPEA or pyridine, and trifluoromethanesulfonic anhydride in dichloromethane. Alternatively the freebase of compound 8 can be used successfully in the subsequent Suzuki coupling. A number of combinations of solvent, boronate, catalyst and ligands can be envisioned for the subsequent Suzuki coupling. In this example, the crude triflate was converted to the crude boronate ester compound 10 using bis(pinacolato)diboron, KOAc and PdCl$_2$(dppf) in DMSO. Subsequent Suzuki coupling directly with 3-amino-6-chloropyridazine using PdCl$_2$ (dppf), Cs$_2$CO$_3$ in a DMF/water mixture afforded the desired compound 2 directly but required a tedious workup and laborious purification to afford pure product. Alternatively, using N,N-di-tert-butoxycarbonyl (Boc) protected 3-amino-6-chloropyridazine (compound 11) in the Suzuki coupling under similar conditions in a mixture of DMSO and water afford compound 12. Compound 11 is readily prepared from commercially available 3-amino-6-chloropyridazine, di-tert-butyl dicarbonate, and DMAP in DMF. Recrystallization of the bis-protected product from IPA/water significantly reduces the mono-boc amino pyridazine intermediate. Work-up of the crude reaction mixture of compound 12 with aqueous LiCl, aqueous NH$_4$OH, or treatment with a suitable metal scavengers such as Si-Thiol (SILICYCLE®), or activated carbon, or recrystallization from alcoholic solvent such as methanol are effective means in reducing the metal contamination of the desired product. The Boc protecting groups are removed under acidic conditions using HCl in an alcoholic solvent, such as methanol or isopropanol to afford the di-HCl salt, compound 13. The free base, compound 2, is produced by crystallization from a mixture of aqueous sodium bicarbonate and methanol.

Alternatively on preparative scale: 3-amino-6-chloropyridazine can be coupled under Suzuki conditions with compound 18, to afford racemic compound 1 (Synthesis Scheme 2). Compound 17, is readily accessible using similar procedures as discussed above and shown in Synthesis Scheme 1, but starting with m-bromobenzaldehyde, where the C-7 bromine atom is the functional handle for installing the heterocycle. Separation of the desired (4S) enantiomer can be carried out on preparative scale using chiral HPLC on a CHIRALCEL® OD column. Subsequent treatment of compound 2 with L-tartaric acid in MeOH generated the L-tartrate salt, in quantitative yield.

Confirmation of Absolute Configuration of Compound 2

Via Asymmetric Synthesis of Compound 7

Proof of the absolute configuration of compound 2 was achieved by executing an asymmetric synthesis of compound 7 and X-ray analysis of intermediate compound 22. (Synthesis Scheme 3). The asymmetric synthesis began with NBS-bromination of m-anisaldehyde to give compound 19 in 87% yield. The ketal compound 20 was prepared from compound 19 using ethylene glycol with camphorsulfonic acid as catalyst in quantitative yield. Heck coupling of compound 20 with (R)-3-acryloyl-4-phenyloxazolidin-2-one using tri-o-tolyl phosphine and palladium acetate gave compound 21 in 81% yield. Grignard addition of the complex formed by 2-naphthyl magnesium bromide and copper (I) bromide-dimethyl sulfide to a solution of compound 21 at −78° C., with warming to room temperature, produced compound 22 in 85% yield, with a d.e. of approximately 98%. The absolute configuration of compound 22 was confirmed by single crystal X-ray crystallography (see structure below). The chiral auxiliary was cleaved by saponification to give carboxylic acid compound 23, which was converted with DPPA and MeOH to the methyl carbamate compound 24 in 59% yield. The ketal of compound 24 was cleaved at 0° C. with HCl. After isolation of the intermediate aldehyde, ring closure under reductive amination conditions gave compound 25 in 60% yield. Reduction of the carbamate group using LiAlH$_4$ provided compound 7 in 70% yield. This compound co-eluted by chiral LC with authentic material prepared by the earlier methods.

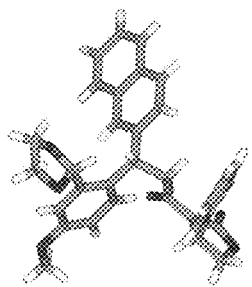

Single Crystal Structure of Compound 22

Synthesis Scheme 1

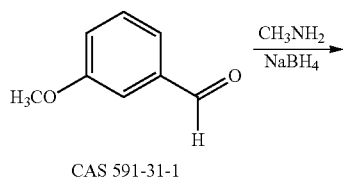

CAS 591-31-1

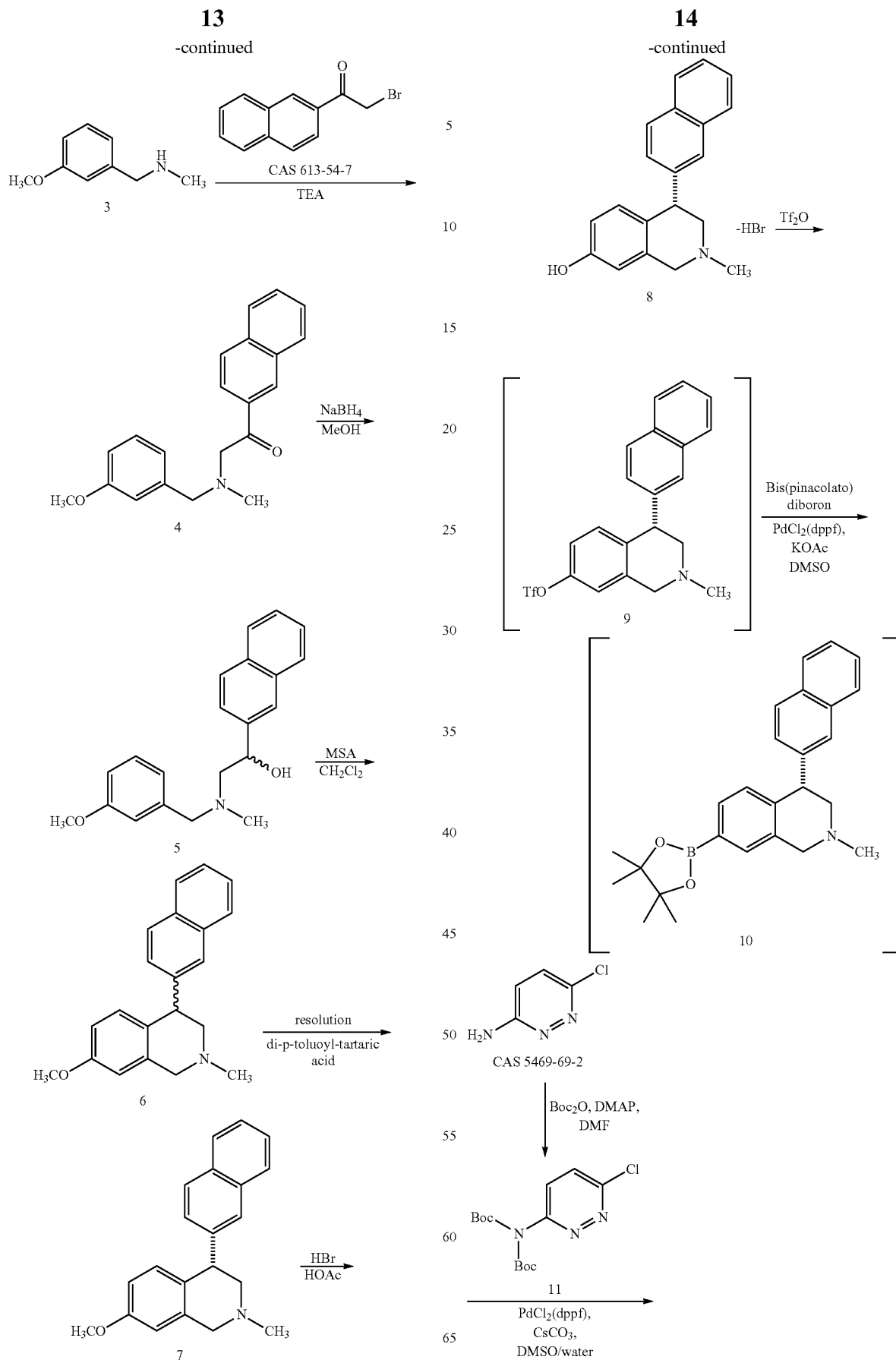

15
-continued
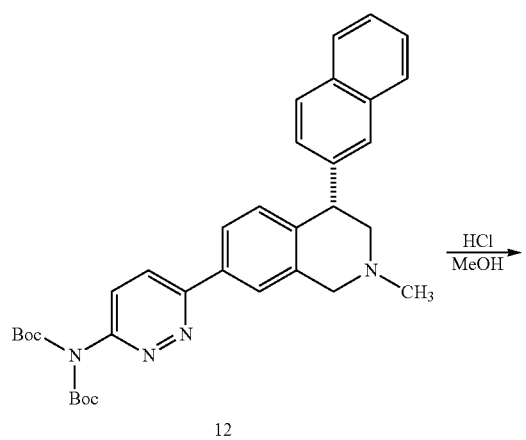
12
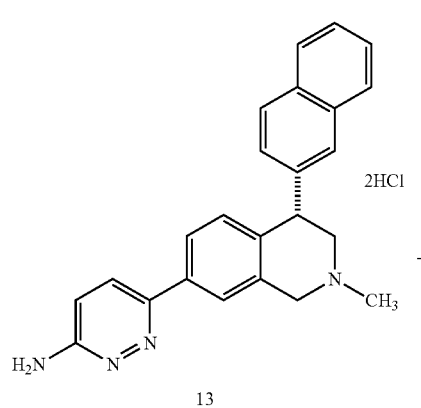
13
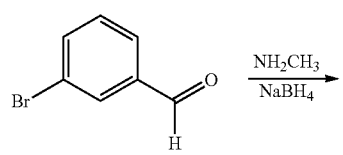
16
-continued
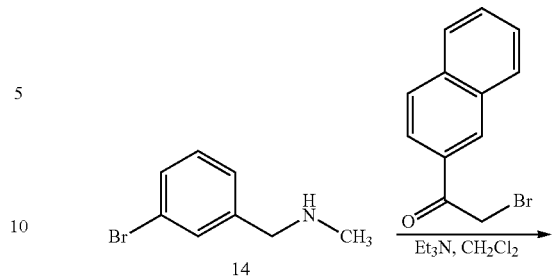
14
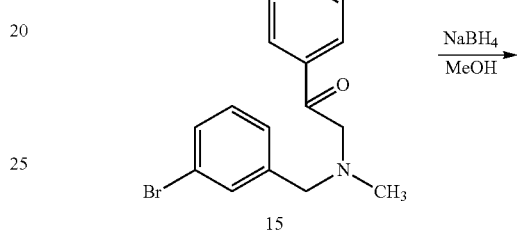
15
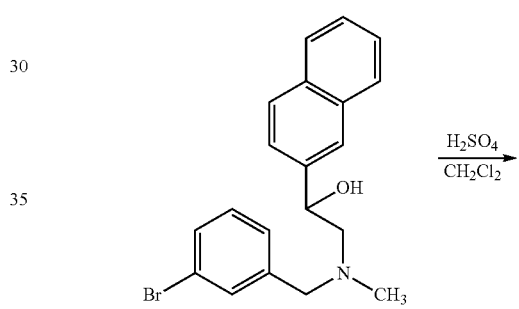
16
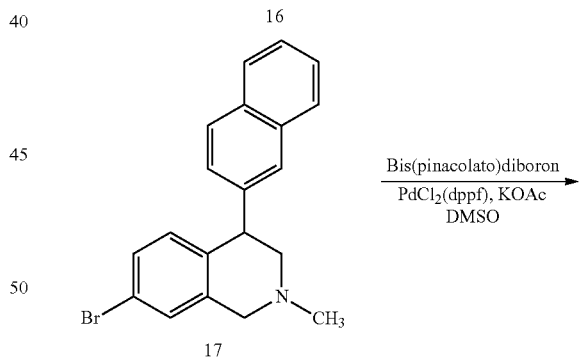
17
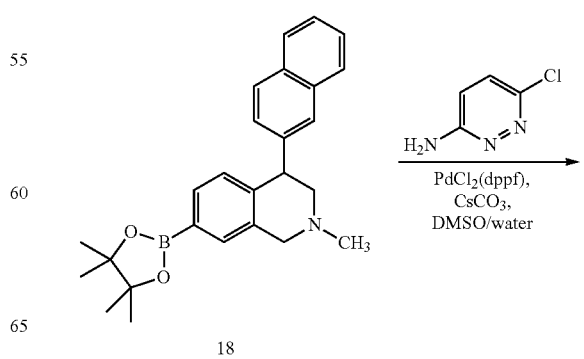
18
2
Synthesis Scheme 2

17
-continued
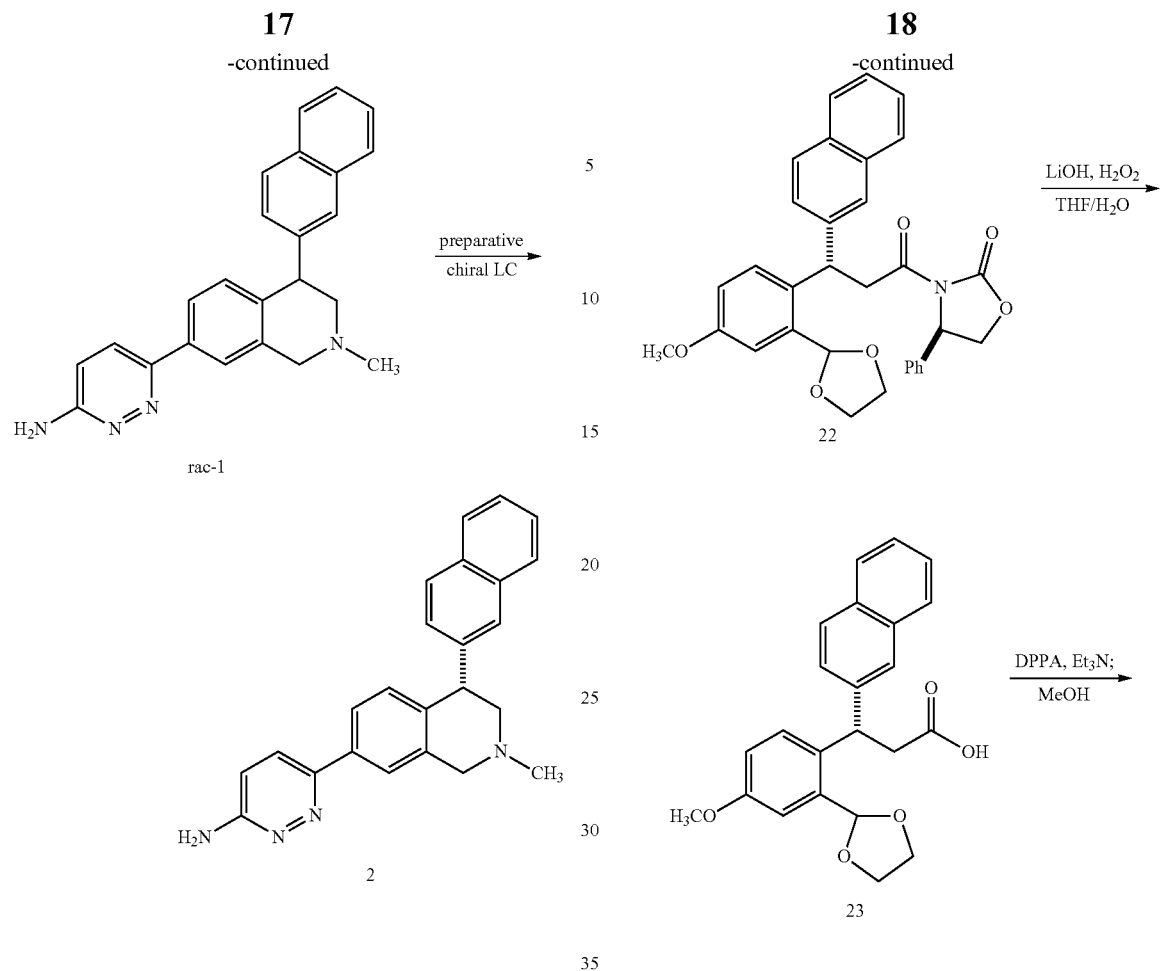
Synthesis Scheme 3
18
-continued
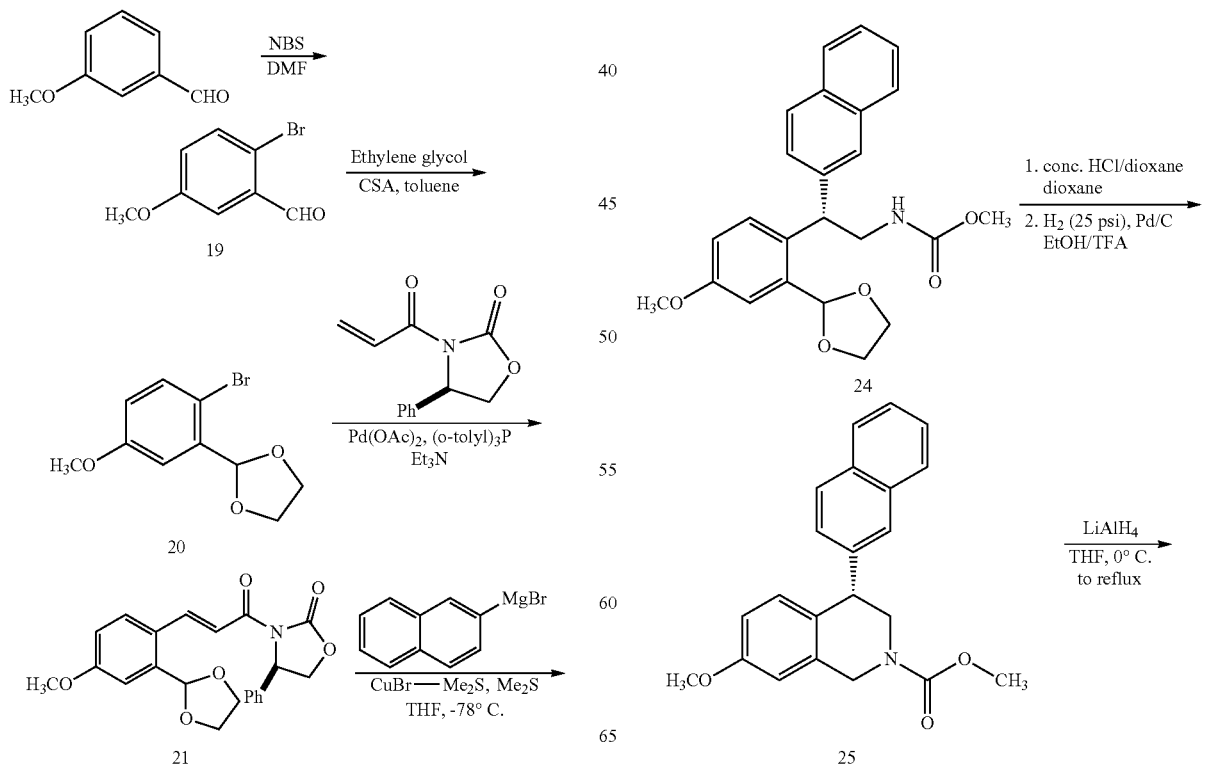

-continued

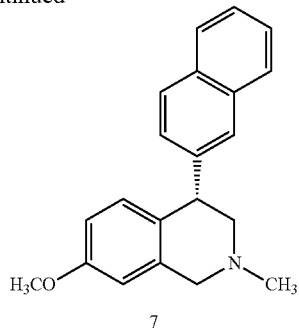

7

EXAMPLES

The following examples are provided for illustrative purposes and are not intended to limit the scope of the claimed invention.

Preparation of 1-(3-methoxyphenyl)-N-methylmethanamine (Compound 3)

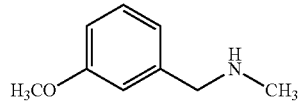

To a solution of m-anisaldehyde (205 g, 1.5 mol) in methanol (800 mL) at room temperature was added methylamine (130 mL of 40% in water, 1.5 mol). The resulting solution was cooled to 0° C. and sodium borohydride (83 g, 2.3 mol) was added in batches. The reaction solution was stirred at 0° C. for 2 h, then warmed to room temperature, concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined methylene chloride extracts were washed with 1:1 water/brine, dried over sodium sulfate and concentrated in vacuo to give additional benzylamine (66.7 g, 29%) as a clear oil: $^1$H NMR (300 MHz, CDCl$_3$) 7.24 (t, J=8.4 Hz, 1H), 6.91-6.78 (m, 3H), 3.81 (s, 3H), 3.73 (s, 2H), 2.46 (s, 3H).

Preparation of 2-((3-methoxybenzyl)(methyl)amino)-1-(naphthalen-2-yl)ethanone (Compound 4)

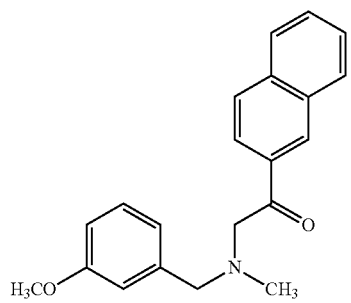 [SMILES: COc1cccc(CN(C)CC(=O)c2ccc3ccccc3c2)c1]

To a solution of α-bromo-2'-acetonaphthone (386.2 g, 1.57 mol) in dichloromethane (2.5 L) at 0° C. was added compound 3 (249.1 g, 1.65 mol) in 30 min, followed by the addition of triethylamine (220.7 mL, 1.57 mmol) in 45 min. After stirring at 0° C. for 40 min, the reaction mixture was warmed to room temperature and stirred overnight. The reaction solution was then washed with water (2×) and the aqueous layer was re-extracted with dichloromethane (2×). The combined organic extract was dried over sodium sulfate and concentrated in vacuo. The ketone, compound 4, was obtained as a reddish oil (513.3 g, quantitative), was used in the next step without further purification: $^1$H NMR (CDCl$_3$, 500 MHz) 8.50 (s, 1H), 8.01 (d, J=8.5 Hz, 1H), 7.92 (d, J=8.0 Hz, 1H), 7.88-7.85 (m, 2H), 7.60-7.54 (m, 2H), 7.26-7.23 (m, 1H), 6.97-6.94 (m, 2H), 6.82 (dd, J=8.0, 2.5 Hz, 1H), 3.88 (s, 2H), 3.75 (s, 3H), 3.69 (s, 2H), 2.42 (s, 3H); ESI MS m/z 320 [M+H]$^+$.

Preparation of 2-((3-methoxybenzyl)(methyl)amino)-1-(naphthalen-2-yl)ethanol (Compound 5)

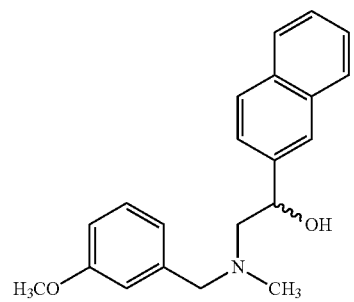 [SMILES: COc1cccc(CN(C)CC(O)c2ccc3ccccc3c2)c1]

A solution of the ketone, compound 4, (512.2 g, 1.57 mol) in methanol (4.0 L) was split equally into two flasks. To each half of the ice-cold solution was added sodium borohydride (33.0 g, 0.87 mol) in batches (~30 min) After the addition, the reaction solution was stirred at 0° C. (internal temperature 10-15° C.) for 50 min before it was quenched slowly with water (~500 mL). The reaction mixture was then concentrated in vacuo to remove most of the organic solvent. The residue obtained from the two batches were combined, extracted with dichloromethane (2×), dried over sodium sulfate and concentrated in vacuo. The alcohol, compound 5, was obtained as a yellow oil (510.4 g, quantitative), and was used in the next step without further purification: $^1$H NMR (500 MHz, CDCl$_3$) δ 7.84-7.80 (m, 4H), 7.47-7.44 (m, 3H), 7.27-7.24 (m, 1H), 6.92-6.83 (m, 3H), 4.92 (dd, J=10.0, 4.0 Hz, 1H), 4.14 (br s, 1H), 3.81 (s, 3H), 3.74 (d, J=13.0 Hz, 1H), 3.53 (d, J=13.0 Hz, 1H), 2.68-2.60 (m, 2H), 2.36 (s, 3H); ESI MS m/z 322 [M+H]$^+$.

Preparation of racemic 7-methoxy-2-methyl-4-(naphthalen-2-yl)-1,2,3,4-tetrahydroisoquinoline (Compound 6)

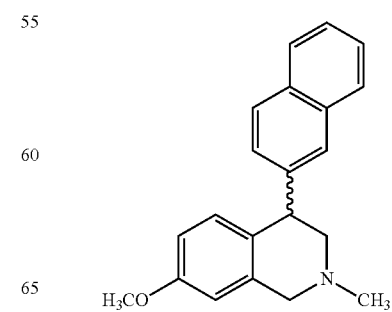

A solution of the alcohol, compound 5, (495 g, 1.54 mol) in dichloromethane (6.0 L) was split equally into two flasks. To each half of the ice-cold solution was added methanesulfonic acid (500 mL, 7.7 mmol) via additional funnel (~1 h). The reaction solution was allowed to slowly warm to room temperature and stirred for 6-8 h before it was cooled to <10° C. and quenched slowly with an aqueous solution of sodium hydroxide (330 g, 8.3 mol in 600 mL of water). The internal temperature during the addition was kept less than 30° C. The organic layer was then separated, washed with water, dried over sodium sulfate and concentrated in vacuo. The crude product from the two batches were combined and purified by flash column chromatography (hexanes/ethyl acetate 88:12 to ethyl acetate/methanol 99.9:0.1) to give compound 6 (280.4 g, 60% over 4 steps) as a thick oil: $^1$H NMR (500 MHz, CDCl$_3$) 7.81-7.74 (m, 3H), 7.68 (s, 1H), 7.47-7.42 (m, 2H), 7.28-7.26 (m, 1H), 6.79 (d, J=8.5 Hz, 1H), 6.80-6.62 (m, 2H), 4.40 (dd, J=8.5, 6.0 Hz, 1H), 3.80-3.78 (m, 1H), 3.77 (s, 3H), 3.65 (d, J=15.0 Hz, 1H), 3.11-3.08 (m, 1H), 2.65 (dd, J=11.5, 6.0 Hz, 1H), 2.45 (s, 3H); ESI MS m/z 304 [M+H]$^+$.

Preparation of racemic 7-methoxy-2-methyl-4-(naphthalen-2-yl)-1,2,3,4-tetrahydroisoquinoline (Compound 6)

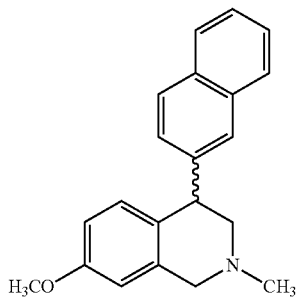 [SMILES: COc1ccc2c(c1)CN(C)CC2c1ccc2ccccc2c1]

Alternatively, the regioisomers can be separated as their respective oxalate salts. A 2.4:1 mixture of regioisomers [547 g, 1.8 mol] in absolute EtOH (2 L) was stirred at ambient temperature as a solution of oxalic acid (162 g, 1.8 mol, ACROS® lot # A0246832) in absolute EtOH (600 mL) was added in one portion (exothermic). The solution became heterogeneous, and after 2 h was filtered to give a light yellow solid [RBM-C-28(1)] that was 90:10 mixture of regioisomers by $^1$H NMR. The filter cake was added to fresh absolute EtOH (6.5 L) and the resulting slurry was heated to 75° C. for 3 hours. The slurry was then cooled to 25° C. and filtered. The filter cake was conditioned under N$_2$ overnight and then added to satd. NaHCO$_3$ (3 L). The product was extracted with EtOAc (3.5 L), and the organic layer was dried (MgSO$_4$) and concentrated to give 355 g of a white solid that was a 96:4 mixture of compound 6 and its regioisomer in 91% yield and 98.4% purity. $^1$H NMR (400 MHz, CDCl$_3$) δ 7.75 (m, 4H), 7.44 (m, 2H), 7.27 (dd, J=8.4, 1.7 Hz, 1H), 6.70 (m, 3H), 4.39 (m, 1H), 3.77 (m, 4H), 3.63 (m, 1H), 3.08 (ddd, J=11.5, 4.3, 1.2 Hz, 1H), 2.64 (dd, J=11.5, 8.9 Hz, 1H), 2.44 (s, 3H).

Preparation of (S)-7-methoxy-2-methyl-4-(naphthalen-2-yl)-1,2,3,4-tetrahydroisoquinoline (Compound 7)

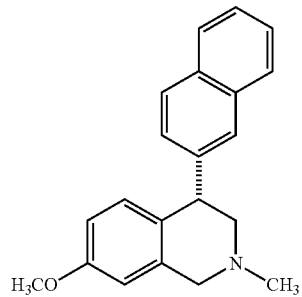 [SMILES: COc1ccc2c(c1)CN(C)CC2c1ccc2ccccc2c1]

To a solution of compound 6 (222.3 g, 0.73 mol) in ethanol (5.5 L) at room temperature was quickly added a solution of di-p-toluoyl-D-tartaric acid (292.2 g, 0.73 mol) in ethanol (1.0 L) with no internal temperature increase noted. The reaction solution was stirred at room temperature. Precipitate started to form within 10 min. After stirring for 2 h, the reaction slurry was filtered and the cake was dried at 60° C. in vacuo for 12 h to give the (4S)-enriched tartrate salt (265.0 g, 52%, with a ratio of enantiomers of approximately 84:16, CHIRALCEL® AD, heptane:IPA:diethyl amine 90:10:0.01). The filtrate was concentrated in vacuo and dried at 60° C. to give the 4R-enriched tartrate salt (238.0 g, 47%, ratio of enantiomers of approximately 3:97). The desired 4S enriched tartrate salt was treated with aqueous sodium hydroxide and separated by preparative chiral chromatography to give pure compound 7. (Preparative chiral chromatography was carried out in two batches of enriched racemate, 117 g and 93 g, respectively. The following conditions were used for the 117 g batch: Thar 350 SFC; Column: CHIRALPAK® AD-H, 5×25 cm; Mobile phase: 30% IPA+0.05% DEA/CO$_2$; Pressure: 100 bar; Temperature: 45° C.; Flow rate: 240 g/min; Solution concentration ~250 mg/ml; Injection amount: 8 mL; Cycle time: 10.5 min/inj; Detector: 254 nM; Throughput: 11-12 g/hr. The sample was dissolved in warm 275 mL MeOH and 95 mL IPA with 0.5 mL DEA added).

Preparation of (S)-2-methyl-4-(naphthalen-2-yl)-1,2,3,4-tetrahydroisoquinolin-7-ol (Compound 8, free base)

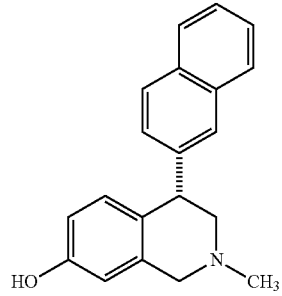 [SMILES: CN1Cc2cc(O)ccc2[C@H](c2ccc3ccccc3c2)C1]

To a solution of compound 7 (42.5 g, 140 mmol) in 48% HBr (200 mL) was added AcOH (100 mL) to give a light yellow suspension. The reaction was heated to give a light yellow solution and stirred at 120° C. for 6 hr (<1.5% starting material left by HPLC), then concentrated. Dichloromethane (500 mL) was added to the residue and the suspension was filtered. The filtrate was neutralized with ice water, 50% NaOH (added slowly) and $Na_2CO_3$ solution to pH of 10. The aqueous layer was extracted with dichloromethane twice. The solid was fully dissolved in dichloromethane and triethylamine (25 mL), and washed with $Na_2CO_3$ solution to pH of 10. The organic layers were combined and washed with $NaHCO_3$ and brine, dried over $Na_2SO_4$ overnight, filtered and concentrated. The crude product compound 8, as the free base, can be used in the next step without further purification.

Preparation of (S)-2-methyl-4-(naphthalen-2-yl)-1,2,3,4-tetrahydroisoquinolin-7-ol (Compound 8, free base)

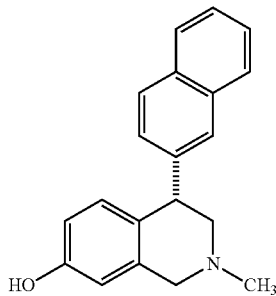 [SMILES: CN1Cc2cc(O)ccc2[C@H](c2ccc3ccccc3c2)C1]

Alternative procedure: To a solution of compound 7 (30.0 g, 99.0 mmol) in acetic acid (150 mL) was added hydrobromic acid (48% solution in water, 450 mL). The reaction solution was flushed with nitrogen and heated at 110° C. (internal temperature) for 3 h, at which time HPLC and MS showed no starting material left. The reaction solution was then cooled to room temperature and concentrated in vacuo. The residue obtained was dissolved in methylene chloride and water, then carefully neutralized with saturated aqueous sodium bicarbonate and sodium hydroxide to pH >8. The organic extract was separated, washed with water and brine, dried over sodium sulfate and concentrated in vacuo to give compound 8 as the freebase, (29.1 g, quantitative yield) as a light yellow solid. The crude product was used in the next step without further purifications: $^1$H NMR (500 MHz, $CDCl_3$) 7.81-7.74 (m, 3H), 7.67 (s, 1H), 7.47-7.42 (m, 2H), 7.30-7.25 (m, 1H), 6.73 (d, J=8.5 Hz, 1H), 6.57-6.52 (m, 2H), 4.38 (dd, J=8.5, 6.0 Hz, 1H), 3.73 (d, J=15.0 Hz, 1H), 3.60 (d, J=15.0 Hz, 1H), 3.11-3.08 (m, 1H), 2.63 (dd, J=11.5, 9.5 Hz, 1H), 2.44 (s, 3H); ESI MS m/z 290 $[M+H]^+$.

Preparation of (S)-2-methyl-4-(naphthalen-2-yl)-1,2,3,4-tetrahydroisoquinolin-7-ol (Compound 8, HBr salt)

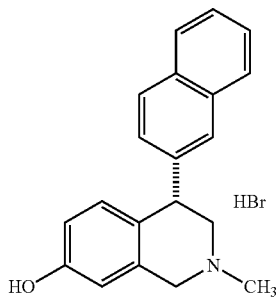 [SMILES: CN1Cc2cc(O)ccc2[C@H](c2ccc3ccccc3c2)C1 ; Br]

Alternatively, the intermediate HBr salt of compound 8 can be isolated and used directly in the next step.

Scaled-up procedure: A mixture of compound 7 (1.0 kg, 1.0 equiv) in AcOH (2.5 L, 2.5 vol) was mechanically stirred and heated at 55-60° C. until the solution was homogeneous. 48 wt % HBr in water (5.0 L, 5.0 vol) was then added in one portion, and the resulting solution was heated to 105° C. for 18 h (the solution became heterogeneous shortly after adding the HBr solution, but became homogeneous after stirring approximately 2 h at 105° C.). The solution was then cooled to 95° C. over 15 minutes. DI water (900 mL) was added over 15 min, and then seeds of authentic Compound 26 (5.0 g) were added. An additional 3.1 L of DI water was then added over 2 hours. The slurry was cooled to 25° C. over 2.5 hours and filtered. The filter cake was conditioned under nitrogen overnight and then added to DI water (4.0 L). The slurry was stirred at ambient temperature for 45 minutes, cooled to 5° C., filtered, conditioned under $N_2$ overnight, and then dried in vacuo to constant weight to give 1.0 kg of compound 8, HBr salt as a white solid in 85% yield and >99% purity. $^1$H NMR (500 MHz, d-DMSO) δ $^1$H NMR (500 MHz, d-DMSO) δ 10.31 (s, 0.85H), 10.11 (br s, 0.15H), 9.60 (s, 1H), 7.91 (m, 4H), 7.54 (m, 2H), 7.30 (d, J=7.5 Hz, 1H), 6.67 (s, 1H), 6.61 (m, 2H), 4.64 (m, 1H), 4.54 (br s, 2H), 3.84 (br s, 1H), 3.62 (t, J=11.2 Hz, 1H), 2.98 (s, 3H).

Preparation of (S)-2-methyl-4-(naphthalen-2-yl)-1,2,3,4-tetrahydroisoquinolin-7-yl trifluoromethanesulfonate (Compound 9)

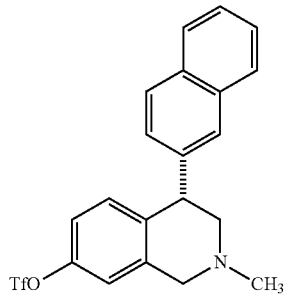 [SMILES: CN1Cc2cc(OS(=O)(=O)C(F)(F)F)ccc2[C@H](c2ccc3ccccc3c2)C1]

To a solution of compound 8, free base (28.9 g, 99.0 mmol) in dichloromethane (820 mL) was added pyridine (10.4 mL, 128.7 mmol). The reaction suspension was stirred for 5 min at room temperature to give a solution. The reaction solution was cooled to 0° C. and trifluoromethanesulfonic anhydride (18.5 mL, 108.9 mmol) was added slowly (~35 min). The reaction mixture was stirred at 0° C. for 45 min before it was quenched with aqueous sodium bicarbonate and extracted with dichloromethane. The combined organic extract was dried over sodium sulfate, filtered and concentrated in vacuo. Compound 9, obtained as a yellow oil, was used in the next step without further purification. $^1$H NMR (500 MHz, $CDCl_3$) 7.83-7.70 (m, 3H), 7.67 (s, 1H), 7.49-7.44 (m, 2H), 7.30-7.23 (m, 1H), 7.04 (d, J=2.05 Hz, 1H), 6.98-6.95 (m, 2H), 4.42 (dd, J=8.0, 6.0 Hz, 1H), 3.81 (dd, J=15.0 Hz, 1H), 3.68 (dd, J=15.0 Hz, 1H), 3.11 (dd, J=11.0, 6.0 Hz, 1H), 2.69 (dd, J=11.0, 3.5 Hz, 1H), 2.46 (s, 3H); ESI MS m/z 422 $[M+H]^+$.

Preparation of (S)-2-methyl-4-(naphthalen-2-yl)-1,2,3,4-tetrahydroisoquinolin-7-yl trifluoromethanesulfonate (Compound 9)

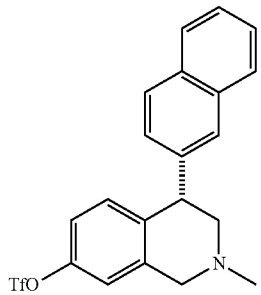 [SMILES: CN1Cc2cc(OS(=O)(=O)C(F)(F)F)ccc2[C@H](c2ccc3ccccc3c2)C1]

Alternative procedure: To a solution of compound 8, HBr salt (40.5 g, 140 mmol) in DCM (1.2 L) was added diisopropylethylamine (48.9 mL, 280 mmol) to give an orange solution. The reaction was cooled to −50° C. Triflic anhydride (Tf$_2$O) (35 mL, 207 mmol) was added in portions until no starting material was left. The reaction was monitored by HPLC in 5 min after each portion of Tf$_2$O addition. When the reaction was finished, aqueous NaHCO$_3$ solution (600 mL) was added. The organic layer was washed with NH$_4$Cl solution (500 mL) and brine (500 mL). The combined organic layer was dried over Na$_2$SO$_4$, filtered and concentrated. DMSO (500 mL) was added and the residual DCM was removed under reduced pressure to give crude product compound 9, which was used directly as is and continued in the example below. HPLC (YMC Pack Pro C18 4.6×50, 4 min): Peak at Tr=2.86 min is starting material. Peak at Tr=3.71 min is product.

Note: A test reaction indicated that the use of an excessive amount of Tf$_2$O may lead to demethylation and other undesired side reactions.

Preparation of (S)-2-methyl-4-(naphthalen-2-yl)-1,2,3,4-tetrahydroisoquinolin-7-yl trifluoromethanesulfonate (Compound 9)

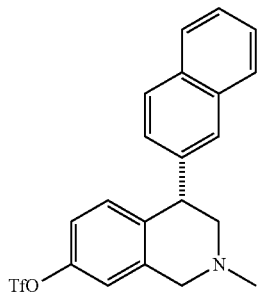 [SMILES: CN1Cc2cc(OS(=O)(=O)C(F)(F)F)ccc2[C@H](c2ccc3ccccc3c2)C1]

Scaled-up procedure: A mixture of compound 8 (1.0 kg, 1.0 equiv.) in DCM (12.4 L) was stirred at room temperature as Et$_3$N (0.90 L, 2.3 equiv) was added over 5 minutes (slightly exothermic). After stirring 20 minutes, the solution was homogeneous. The reactor was then cooled to −55 to −60° C. in a dry ice/IPA bath, and Tf$_2$O (0.56 L, 1.2 equiv.) was added over 2.5 hours, maintaining an internal temperature of <−50° C. After the addition was complete, the mixture was stirred for 20 minutes at −50° C. and HPLC analysis indicated the reaction was complete. The solution was warmed to −10° C. and 10% aq. NaHCO$_3$ (6.2 L) was added in one portion. The resulting mixture was then warmed to 20° C. and stirred for 30 minutes. The layers were then separated, and the organic phase was washed with DI water (6.2 L) and concentrated under reduced pressure to give 1.2 kg of the crude product compound 9 as a dark red oil in >100% yield due to residual DCM, but with 73.5% purity.

Preparation of di-tert-butyl(6-chloropyridazin-3-yl)imidodicarbonate (Compound 11)

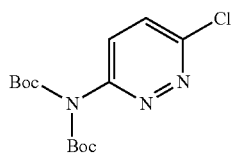 [SMILES: CC(C)(C)OC(=O)N(C(=O)OC(C)(C)C)c1ccc(Cl)nn1]

To a solution of 6-chloropyridazin-3-amine (75 g, 579 mmol) in DMF (600 ml) was added di-tert-butyl dicarbonate (278 g, 1274 mmol) and DMAP (0.6 g, 4.91 mmol) to give a suspension. The mixture was heated to 50° C. to give an orange solution and the reaction temperature reached 75° C. by itself with gas bubbles generated. The heating mantel was removed and the reaction was cooled to 55° C. slowly. Then the reaction was stirred at 55° C. with heating for 2 h to give a dark brown solution. After the reaction was cooled to room temperature, the reaction solution was poured to a 4 L beaker and water (3 L) was added to give a light brown suspension. The yellow precipitate was collected by filtration and washed with water (4 L). No product was dissolved in water. The solid was dried in oven overnight to give product (152.2 g, 80% yield) as a light yellow solid.

Preparation of di-tert-butyl(6-chloropyridazin-3-yl)imidodicarbonate (Compound 11)

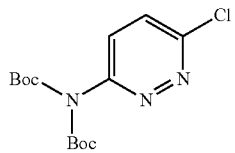 [SMILES: CC(C)(C)OC(=O)N(C(=O)OC(C)(C)C)c1ccc(Cl)nn1]

Scaled-up procedure: A mixture of 3-chloro-6-aminopyridazine (500 g, 1.0 equiv) and DMAP (3.77 g, 0.008 equiv) in DMF (3.5 L) was heated and stirred at 55° C. for 20 minutes, until the mixture became homogeneous. A solution of Boc$_2$O (2.2 equiv) in DMF (500 mL) was prepared separately and then added in one portion to the batch, causing an endothermic event. The reaction solution was monitored by HPLC while stirring at 55° C., and after 5 h, the reaction was deemed complete. The solution was cooled to room temperature and then slowly poured into DI water (4.4 L), causing precipitation. The mixture was stirred for 10 minutes and then filtered. The resulting brown solid was conditioned overnight under nitrogen. A mixture of the crude product in 2-propanol (3.5 L) was heated and stirred at 65° C. until the mixture became homogeneous. DI water (3.5 L) was then added over 30 min (temperature was not controlled). The reaction mixture was cooled to room temperature and then filtered to give 805 g compound 11 as a light brown solid in 63% yield, and 99.7% purity. $^1$H NMR (300 MHz, d-DMSO) δ 8.00 (q, J=9.0 Hz, 2H), 1.40 (s, 18H).

Preparation of (S)-di-tert-butyl-(6-(2-methyl-4-(2-naphthyl)-1,2,3,4-tetrahydro-7-isoquinolinyl)-3-pyridazinyl)imidodicarbonate (Compound 12)

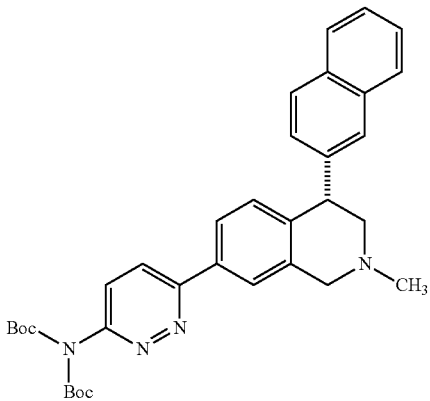 [SMILES: CN1Cc2cc(-c3ccc(N(C(=O)OC(C)(C)C)C(=O)OC(C)(C)C)nn3)ccc2[C@H](c2ccc3ccccc3c2)C1]

(Continued from example above: To the solution of crude compound 9 (~140 mmol) (prepared above) in DMSO (800 mL) in a 5 L three-necked round bottom flask was added bis(pinacolato)diboron (42.7 g, 168 mmol) and potassium acetate (41.2 g, 420 mmol). The mixture was stirred at room temperature under nitrogen for 5 min followed by the addition of dichloro[1,1'-ferrocenylbis(diphenyl-phosphine)]palladium(II) dichloromethane (Pd(dppf)Cl$_2$.CH$_2$Cl$_2$) (18.29 g, 22.40 mmol). The reaction was stirred at 80° C. for 0.5 h. HPLC showed no starting material remaining HPLC (YMC Pack Pro C18 4.6×50, 4 min): Peak at Tr=3.73 min is starting material. Peaks at Tr=3.85 and 2.93 min are the product compound 10 (LCMS=400.31 [M+H]) and boronic acid (LCMS=318.28 [M+H]), respectively.

To the solution of compound 10 prepared above was added compound 11(175 mmol), Pd(dppf)Cl$_2$.CH$_2$Cl$_2$) (18.29 g, 22.4 mmol), DMSO (400 mL), Cs$_2$CO$_3$ (137 g, 420 mmol) and water (250 mL) at 80° C. The reaction was stirred at 80° C. for 2 h. The reaction was cooled to room temperature and diluted with water (6 L). The black precipitate was collected by filtration, dissolved in DCM (1 L), and washed with 10% LiCl aqueous solution (500 mL). The aqueous layer was back extracted with DCM (400 mL). The combined organic layers were filtered through a CELITE® pad and concentrated. Crude product compound 12 was obtained as a dark grey solid (57.4 g, 71% yield, 98% purity) by crystallization in MeOH (300 ml). HPLC (YMC Pack Pro C18 4.6×50, 4 min): Peak at Tr=3.80 is the product compound 12. LCMS=567.33 [M+H].

Purification of (S)—N,N-di-tert-butyl-(6-(2-methyl-4-(2-naphthyl)-1,2,3,4-tetrahydro-7-isoquinolinyl)-3-pyridazinyl)imidodicarbonate (Compound 12)

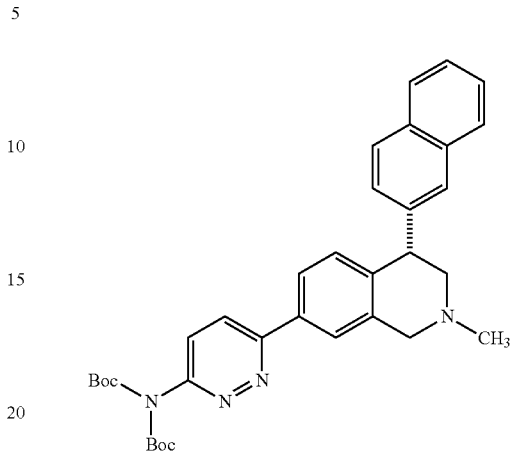

1. Several batches was combined together for purification. To a solution of crude compound 12 (120 g, 98% purity, dark grey solid) in dichloromethane (1 L) was added activated carbon (50 g). The suspension was refluxed for 1 h and the charcoal was filtered off through a CELITE® pad. The filtrate was concentrated and the residue was recrystallized in MeOH (1 L, reflux 30 min). The solution was cooled to room temperature and the grey crystals were collected by filtration. The recrystallization was repeated two times.

2. The solid was de-colored with charcoal in dichloromethane and recrystallized in MeOH again to give a beige solid.

3. The solid was dissolved in dichloromethane (1 L) and washed with ammonium hydroxide solution (100 ml concentrated NH$_4$OH+900 ml water) to primarily remove residual iron. The middle black suspension layer between the aqueous layer and dichloromethane layer was removed with the use of a separation funnel. The light yellow dichloromethane layer was dried over Na$_2$SO$_4$ and concentrated. The residue was recrystallized in MeOH (500 ml) again to give off-white color solid.

4. The solid was dissolved in dichloromethane (500 ml) and the solution was concentrated. The residue was recrystallized in MeOH (500 ml) and the product was collected by filtration as a white solid. First fraction, 95 g, >99% purity, white solid; second fraction, 10 g, 98% purity from last MeOH mother liquid; third fraction, 1 g, 90% purity from former mother liquid. $^1$H NMR (500 MHz, CDCl$_3$) 7.96 (s, 1H), 7.66-7.89 (m, 6H), 7.40-7.53 (m, 3H), 7.28 (d, J=7.15 Hz, 1H), 7.04 (d, J=8.25 Hz, 1H), 4.46-4.56 (m, 1H), 3.84 (dd, J=80.56, 15.12 Hz, 2H), 3.15 (dd, J=11.55, 6.05 Hz, 1H), 2.71 (dd, J=11.55, 8.80 Hz, 1H), 2.49 (s, 3H), 1.46 (s, 18H). $^{13}$C NMR (126 MHz, CDCl$_3$) ppm 157.78, 154.91, 150.59, 141.51, 139.60, 136.19, 133.48, 132.47, 130.24, 128.18, 127.84, 127.67, 127.63, 127.13, 126.08, 125.77, 125.63, 125.17, 125.07, 125.01, 83.92, 61.43, 58.44, 46.00, 45.90, 27.88.

Preparation of (S)—N,N-di-tert-butyl-(6-(2-methyl-4-(2-naphthyl)-1,2,3,4-tetrahydro-7-isoquinolinyl)-3-pyridazinyl)imidodicarbonate (Compound 12)

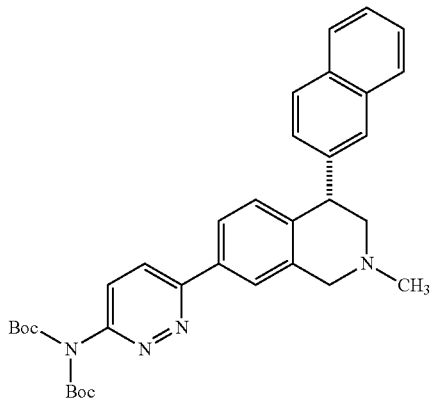 [SMILES: CN1Cc2cc(-c3ccc(N(C(=O)OC(C)(C)C)C(=O)OC(C)(C)C)nn3)ccc2[C@H](c2ccc3ccccc3c2)C1]

Scaled-up procedure: A solution of compound 9 (1.18 kg, 1.0 equiv) in DMSO (16.5 L, 14 vol) was stirred at ambient temperature in a 50-L jacketed reactor as bis-pinacolato diboron (0.85 kg, 1.2 equiv) and KOAc (0.82 kg, 3.0 equiv) were added. The heterogeneous mixture was sparged with a strong stream of nitrogen for 1.5 hours. PdCl$_2$(dppf) (60 g, 0.025 equiv) was then added and the mixture was heated and stirred at 85° C. under nitrogen. After 5 hours, HPLC analysis indicated the reaction had stalled at ~67% conversion, so an additional 10 g of PdCl$_2$(dppf) was added. After 2 h, the reaction had again stalled at 75% conversion. The solution was sparged with N$_2$ for 30 min, and sparging was continued throughout the rest of the reaction. An additional 10 g of PdCl$_2$(dppf) was added, and the reaction was complete within 2.5 h to afford a reaction mixture containing compound 10. A solution of Cs$_2$CO$_3$ (2.74 kg, 3.0 equiv) in DI water (4.2 L) that had been sparged with a strong stream of N$_2$ for 1.5 hours was then added in one portion. A slurry of compound 11 (1.15 kg, 1.25 equiv) in DMSO (6.5 L) that had been sparged with a strong stream of N$_2$ for 1.5 hours was then added in one portion (delayed exotherm). A final charge of PdCl$_2$(dppf) (60 g) was added, and the reaction mixture was stirred at 85° C. for 12 h and then cooled to 25° C. DI water (5.0 L) was added, and after stirring for 1 hour, the mixture was filtered to give a brown solid, which was conditioned under N$_2$ overnight.

The filter cake was dissolved in DCM (18 L) and the organic layer was washed with a 10% aqueous LiCl solution (18 L) and a 10% aqueous NH$_4$OH solution (18 L). The DCM layer was concentrated under reduced pressure to leave a brown solid. MeOH (6 L) was added and the slurry was stirred and heated at 55° C. for 1 hour. It was then cooled to 25° C. and EtOAc (12 L) was added. The resulting slurry was stirred for 1 hour, filtered, and the filter cake was conditioned under N$_2$ overnight to give 750 g of a grey solid. ICP analysis indicated the palladium content was ~2300 ppm. The solid was then dissolved in DCM (3.75 L) and Si-thiol (1.50 kg, 2 wt equiv, SILICYCLE® lot #10347) was added. The mixture was vigorously stirred at 30-35° C. for 4.5 hours. The mixture was cooled to room temperature and then filtered. The solid Si-thiol was then rinsed with DCM (7.5 L) and the combined dark brown filtrates were transferred to a Rotovap bulb through two 1.2 micron filters and concentrated under reduced pressure to give an off-white solid. ICP analysis indicated the palladium content was 160 ppm. The batch was re-dissolved in DCM (3.75 L) and Si-thiol (1.50 kg, 2 wt equiv) was added. After stirring for 4.5 hours at 30-35° C., the mixture was cooled to room temperature and filtered. The solid Si-thiol was rinsed with DCM (7.5 L), and the combined yellow filtrates were transferred to a Rotovap bulb through a 1.2 micron filter and concentrated under reduced pressure to give an off-white solid. ICP analysis indicated the palladium content was 3 ppm. EtOAc (4.2 L) was then added to the solid and the resulting slurry was stirred at ambient temperature for 1 hour and then filtered. The filter cake was rinsed with EtOAc (500 mL). The filter cake was conditioned under N$_2$ for 2 days to give 715 g of a compound 12 as a white solid in 47% yield and >99% purity. $^1$H NMR (500 MHz, d-DMSO) δ 8.31 (d, J=9.1 Hz, 1H), 8.02 (d, J=1.3 Hz, 1H), 7.87 (m, 5H), 7.79 (s, 1H), 7.48 (m, 2H), 7.39 (dd, J=8.5, 1.5 Hz, 1H), 7.01 (d, J=8.2 Hz, 1H), 4.49 (t, J=6.3 Hz, 1H), 3.78 (m, 2H), 3.02 (dd, J=11.5, 6.6 Hz, 1H), 2.73 (dd, J=11.4, 7.1 Hz, 1H), 2.39 (s, 3H), 1.41 (s, 18H).

Preparation of (S)-2-methyl-4-(naphthalen-2-yl)-7-(4,4,5,5-tetramethyl-1,3,2-dioxaborolan-2-yl)-1,2,3,4-tetrahydroisoquinoline (Compound 10)

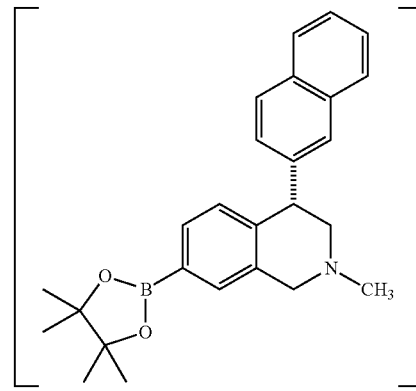

Alternative procedure: To a mixture of the triflate compound 9 (99.0 mmol), bis(pinacolato)diboron (30.2 g, 118.8 mmol) and potassium acetate (29.1 g, 297.0 mmol) was added DMSO (725 mL). The resulting solution was purged with argon for 10 min, and then dichloro[1,1'-bis(diphenylphosphino)ferrocene]palladium(II) dichloromethane adduct (6.47 g, 7.92 mmol) was added. The reaction solution was degassed again with argon for 5 min, heated at 82° C. (oil bath) for 1 h and then cooled to room temperature and poured into water (1.0 L). The mixture was extracted with ethyl acetate (800 mL) and the organic extract was separated and washed with water (2×) and brine, dried over sodium sulfate and concentrated in vacuo. The crude boronate ester compound 10 (48.0 g), obtained as a brown foam, was used in the next step without further purification: ESI MS m/z 400 [M+H]$^+$.

Preparation of (S)-6-(2-methyl-4-(naphthalen-2-yl)-1,2,3,4-tetrahydroisoquinolin-7-yl)pyridazin-3-amine (Compound 2)

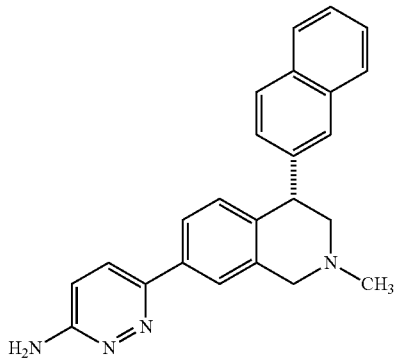

Alternative procedure directly from 3-amino-6-chloropyridazine: To a mixture of the boronate ester compound 10 (23.0 g, 47.4 mmol), 3-amino-6-chloropyridazine (9.2 g, 71.1 mmol) and cesium carbonate (46.3 g, 142.2 mmol) were added DMF (464 mL) and water (116 mL). The reaction solution was flushed with argon for 10 min, and then dichloro[1,1′-bis(diphenylphosphino)ferrocene]palladium(II) dichloromethane adduct (3.9 g, 4.74 mmol) was added. The mixture was flushed with argon for 5 min and heated at 80° C. for 1 h. The reaction solution was cooled to room temperature, diluted with ethyl acetate, washed with 1:1 brine and water (2×), dried over sodium sulfate and concentrated in vacuo. The crude product was purified by flash column chromatography (99:0.9:0.1 to 94:5.4:0.6 ethyl acetate/methanol/concentrated ammonium hydroxide). This partially purified product (14.8 g as a brown solid) was stirred with ethyl acetate (120 mL) under argon for 12 h and filtered to give compound 2 (12.5 g, 72%) as a brown solid: $^1$H NMR (500 MHz, CDCl$_3$) 7.82-7.76 (m, 4H), 7.71 (s, 1H), 7.61-7.57 (m, 2H), 7.47-7.43 (m, 2H), 7.30 (dd, J=8.0, 1.5 Hz, 1H), 6.99 (d, J=8.0 Hz, 1H), 6.80 (d, J=9.5 Hz, 1H), 4.71 (br s, 2H), 4.50 (t, J=7.0 Hz, 1H), 3.89 (d, J=15.0 Hz, 1H), 3.74 (d, J=14.5 Hz, 1H), 3.14 (dd, J=11.5, 6.0 Hz, 1H), 2.70 (dd, J=11.5, 9.0 Hz, 1H), 2.48 (s, 3H); ESI MS m/z 367 [M+H]$^+$.

Preparation of (S)-6-(2-methyl-4-(naphthalen-2-yl)-1,2,3,4-tetrahydroisoquinolin-7-yl)pyridazin-3-amine dihydrochloride (Compound 13)

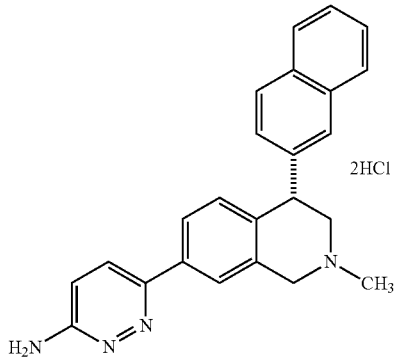 [SMILES: CN1Cc2cc(-c3ccc(N)nn3)ccc2[C@H](c2ccc3ccccc3c2)C1]

Compound 12 (193 g, 341 mmol) was dissolved in 2.5 M hydrochloride in ethanol (1088 ml, 2720 mmol). The solution was heated at 75° C. for 1 h. The resulted suspension was cooled to room temperature and diluted with EtOAc (2 L). The white solid was collected by filtration, washed with EtOAc (1 L). The white solid was dried at 40° C. overnight under reduced pressure to give compound 13 (143 g, 96% yield, 99.8% purity): $^1$H NMR (500 MHz, DMSO-d$_6$) ppm: 8.77 (s-broad, 2H); 8.37 (d, J=9.71 Hz, 1H); 7.95 (overlap, 1H); 7.94 (m, 2H); 7.94 (overlap, 1H); 7.91 (s, 1H); 7.76 (d, J=8.01 Hz, 1H); 7.66 (d, J=9.71 Hz, 1H); 7.56 (m, 1H); 7.55 (m, 1H); 7.33 (broad, 1H); 6.94 (broad, 1H); 4.92 (m, 1H); 4.66 (s-broad, 2H); 3.85 (m, 1H); 3.73 (m, 1H); 2.97 (s, 3H). HRMS [M+H]$^+$=367.19202.

Preparation of (S)-6-(2-methyl-4-(naphthalen-2-yl)-1,2,3,4-tetrahydroisoquinolin-7-yl)pyridazin-3-amine (Compound 2)

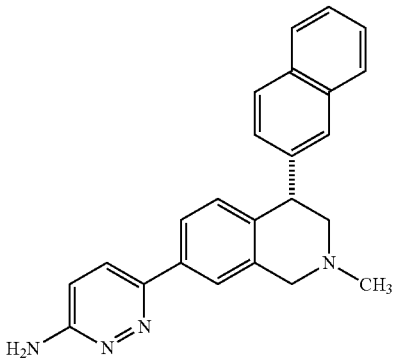 [SMILES: CN1Cc2cc(-c3ccc(N)nn3)ccc2[C@H](c2ccc3ccccc3c2)C1]

A solution of compound 13 (30.0 g, 0.68 mmol) in 1:1 (v/v) MeOH/H$_2$O (900 mL) was filtered through a glass-sintered funnel. The filtrate was then stirred at room temperature as a saturated solution of aqueous NaHCO$_3$ (45 mL) was slowly added over 30 minutes, causing the solution to turn cloudy. Previously prepared seed crystals (0.10 g) were then added to the batch in one portion. Additional saturated aqueous NaHCO$_3$ (555 mL) was added to the reaction mixture over 1.5 h. The slurry was filtered to afford a wet cake. The wet filter cake was then suspended in 8:2 (v/v) H$_2$O/MeOH (250 mL) and the resulting slurry was stirred for 3 hours and then filtered. The filter cake was washed with 8:2 (v/v) H$_2$O/MeOH (100 mL) and the obtained white solid was dried in vacuo at 50° C. for 30 h to give compound 2 (23.2 g, 93% yield): $^1$H NMR (d$_6$-DMSO, 300 MHz) 7.80-7.90 (m, 3H), 7.74-7.78 (m, 3H), 7.65 (dd, J=8.6; 2.1 Hz, 1H), 7.43-7.53 (m, 2H), 7.38 (dd, J=8.6; 2.1 Hz, 1H), 6.90 (d, J=8.0 Hz, 1H), 6.83 (d, J=9.1 Hz, 1H), 6.45 (s, 2H), 4.43 (t, J=5.9 Hz, 1H), 3.73 (s, 2H), 3.00 (dd, J=10.7, 5.4 Hz, 1H), 2.70 (dd, J=11.3; 7.5 Hz, 1H), 2.37 (s, 3H); $^{13}$C NMR (75 MHz, DMSO) ppm 159.69, 149.65, 142.55, 136.95, 135.62, 134.79, 132.93, 131.83, 129.47, 127.67, 127.46, 127.40, 127.28, 127.16, 125.98, 125.47, 125.15, 123.32, 123.06, 114.12, 60.63, 57.82, 45.55, 44.69, 40.34.

Preparation of (S)-6-(2-methyl-4-(naphthalen-2-yl)-1,2,3,4-tetrahydroisoquinolin-7-yl)pyridazin-3-amine dihydrochloride (Compound 13)

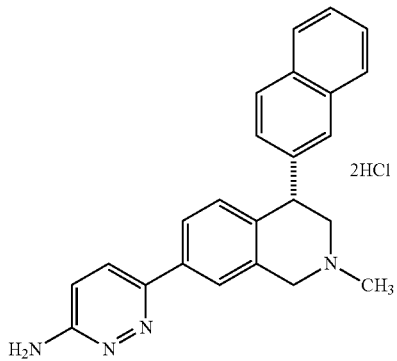 [SMILES: CN1Cc2cc(-c3ccc(N)nn3)ccc2[C@H](c2ccc3ccccc3c2)C1]

Scaled-up procedure: A mixture of compound 12 (750 g, 1.0 equiv) in IPA (3.75 L) was stirred at room temperature as 5-6 N HCl in IPA (3.75 L) was added over 5 minutes (slightly exothermic). The mixture was then heated to 70° C. and held for 18 h, during which time the mixture became a homogeneous yellow solution, and then a white slurry. HPLC analysis indicated the reaction was complete. The mixture was cooled to 25° C. and EtOAc (8 L) was then added in one portion. After stirring for 1 hour, the mixture was filtered to give 555 g of a compound 13 as a white solid in 95% yield, and with >99% purity. $^1$H NMR (500 MHz, d-DMSO) δ 12.05 (br s, 1H), 8.83 (br s, 2H), 8.38 (d, J=9.7 Hz, 1H), 7.94 (m, 5H), 7.76 (d, J=8.1 Hz, 1H), 7.69 (d, J=9.7 Hz, 1H), 7.55 (m, 2H), 7.33 (s, 1H), 6.93 (d, J=5.3 Hz, 1H), 4.92 (m, 1H), 4.68 (br s, 2H), 3.85 (m, 1H), 3.76 (m, 1H), 3.55 (br s, 1H), 2.97 (s, 3H).

Preparation of (S)-6-(2-methyl-4-(naphthalen-2-yl)-1,2,3,4-tetrahydroisoquinolin-7-yl)pyridazin-3-amine dihydrochloride (Compound 13)

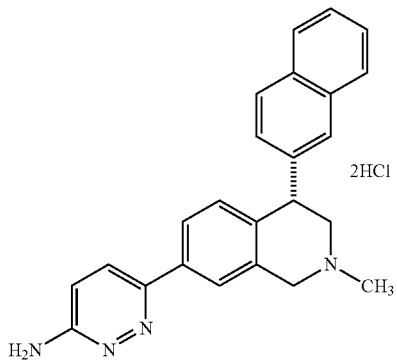 [SMILES: CN1Cc2cc(-c3ccc(N)nn3)ccc2[C@H](c2ccc3ccccc3c2)C1]

Alternative procedure for preparation of compound 13, bis-HCl salt, from compound 2, Form N-1 free base: To a solution of compound 2 (35.9 g, 98.0 mmol) in ethanol (750 mL) at room temperature was added concentrated HCl (28.7 mL) via additional funnel. The solution was heated at 80° C. and additional EtOH (500 mL) and water (55 mL) were added. After all the additions, the reaction mixture was stirred at 80° C. for 30 min upon which all solids dissolved. The solution was then filtered and the filtrate was allowed to cool to room temperature and stand overnight. The precipitate formed was collected by filtration and dried at 40° C. in vacuo for 5 h to give the desired bis-HCl salt compound 13 (28.7 g) as an off-white solid. $^1$H NMR (500 MHz, DMSO-d$_6$) ppm: 8.77 (s-broad, 2H); 8.37 (d, J=9.71 Hz, 1H); 7.95 (overlap, 1H); 7.94 (m, 2H); 7.94 (overlap, 1H); 7.91 (s, 1H); 7.76 (d, J=8.01 Hz, 1H); 7.66 (d, J=9.71 Hz, 1H); 7.56 (m, 1H); 7.55 (m, 1H); 7.33 (broad, 1H); 6.94 (broad, 1H); 4.92 (m, 1H); 4.66 (s-broad, 2H); 3.85 (m, 1H); 3.73 (m, 1H); 2.97 (s, 3H). HRMS [M+H]$^+$=367.19202.

Preparation of (S)-6-(2-methyl-4-(naphthalen-2-yl)-1,2,3,4-tetrahydroisoquinolin-7-yl)pyridazin-3-amine (Compound 2)

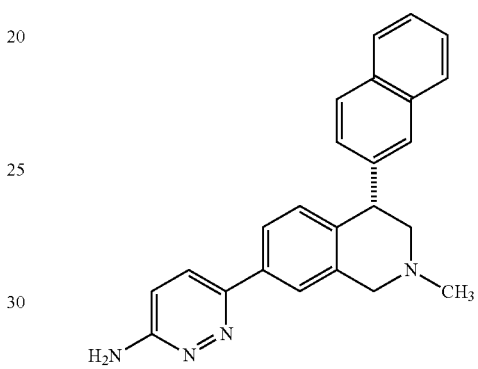

A solution of compound 13 (550 g, 1.0 equiv) in 1:1 MeOH/DI water (16.5 L) was passed through a 1.2 micron in-line filter. The solution was stirred at ambient temperature as a 10% aq. NaHCO$_3$ solution was slowly added. The batch became cloudy after 350 mL of the NaHCO$_3$ solution had been added. Seed crystals (10.5 g) were then added, and the mixture was stirred for an additional 1 hour. More of the NaHCO$_3$ solution (4 L) was added over 40 minutes. After the addition was complete, the mixture was stirred for 2 hours and then filtered. After conditioning on the filter under N$_2$ for 1 hour, the wet filter cake was re-suspended in 8:2 DI water/MeOH (5.5 L), stirred for 2 hours, and then filtered. The filter cake was conditioned under N$_2$ for 48 hours and then dried in vacuo at 35° C. for 48 hours to give 450 g of the compound 2 as a white solid in 96% yield and >99% purity.

Examples for Synthesis Scheme 3

Asymmetric Synthesis of Compound 7

Preparation of 2-bromo-5-methoxybenzaldehyde (Compound 19))

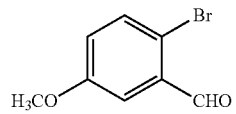

To a solution of m-anisaldehyde (55.4 g, 0.41 mol) in DMF (400 mL) was added a solution of N-bromosuccinimide (124.0 g, 0.69 mol) dropwise at room temperature. After the addition, the reaction solution was stirred at room temperature for 12 h, then poured into a mixture of ice and water and stirred for 10 min. The precipitate was collected by filtration and dissolved in ethyl acetate. The resulting solution was washed with water (2×) and brine, dried over sodium sulfate and concentrated in vacuo to give compound 19 (76.4 g, 87%) as an off-white solid: $^1$H NMR (CDCl$_3$, 500 MHz) 10.32 (s, 1H), 7.53 (d, J=8.5 Hz, 1H), 7.42 (d, J=3.5 Hz, 1H), 7.04 (dd, J=9.0, 3.0 Hz, 1H), 3.85 (s, 3H).

Preparation of 2-(2-bromo-5-methoxyphenyl)-1,3-dioxolane (Compound 20)

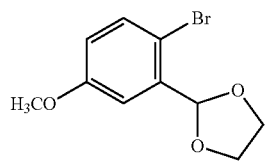 [SMILES: COc1ccc(Br)c(C2OCCO2)c1]

To a solution of compound 19 (50.0 g, 0.23 mol) in toluene (650 mL) were added ethylene glycol (14.2 mL, 0.26 mol) and camphorsulfonic acid (10.7 g, 46 mmol). The reaction solution was heated under reflux with a Dean-Stark trap for 6 h and then cooled to room temperature and diluted with ethyl acetate (300 mL). The resulting solution was washed with aqueous saturated sodium bicarbonate and brine, dried over sodium sulfate and concentrated in vacuo to give compound 20 (61.5 g, quantitative) as a yellow oil: $^1$H NMR (CDCl$_3$, 500 MHz) 7.44 (d, J=8.5 Hz, 1H), 7.15 (d, J=3.5 Hz, 1H), 6.79 (dd, J=8.5, 3.0 Hz, 1H), 6.04 (s, 1H), 4.18-4.06 (m, 4H), 3.81 (s, 3H).

Preparation of (R,E)-3-(3-(2-(1,3-dioxolan-2-yl)-4-methoxyphenyl)acryloyl)-4-phenyloxazolidin-2-one (Compound 21)

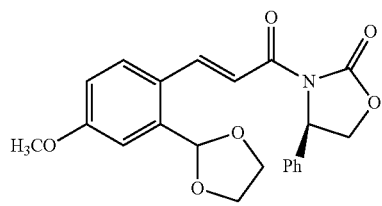 [SMILES: COc1ccc(/C=C/C(=O)N2C(=O)OC[C@H]2c2ccccc2)c(C2OCCO2)c1]

A mixture of compound 20 (2.6 g, 10.0 mmol), (R)-3-acryloyl-4-phenyloxazolidin-2-one (2.2 g, 10.0 mmol), tri-o-tolyl phosphine (0.30 g, 1.0 mmol) and palladium acetate (0.11 g, 0.5 mmol) in triethylamine (35 mL) under argon was stirred under reflux for 90 min. The resulting reaction mixture was cooled to room temperature and concentrated in vacuo. The residue obtained was purified by flash column chromatography (hexanes/ethyl acetate 95:5 to 60:40) to give compound 21 (3.2 g, 81%) as a light yellow oil: $^1$H NMR (500 MHz, CDCl$_3$) 8.19 (d, J=15.5 Hz, 1H), 7.81 (d, J=15.5 Hz, 1H), 7.40 (d, J=8.5 Hz, 1H), 7.41-7.30 (m, 5H), 7.17 (d, J=3.0 Hz, 1H), 6.91 (dd, J=8.5, 3.0 Hz, 1H), 6.01 (s, 1H), 5.54 (dd, J=9.0, 3.5 Hz, 1H), 4.73 (t, J=9.0 Hz, 1H), 4.30 (dd, J=9.0, 4.0 Hz, 1H), 4.32-4.28 (m, 2H), 4.13-4.10 (m, 2H), 3.85 (s, 3H).

Preparation of (R)-3-((S)-3-(2-(1,3-dioxolan-2-yl)-4-methoxyphenyl)-3-(naphthalen-2-yl)propanoyl)-4-phenyloxazolidin-2-one (Compound 22)

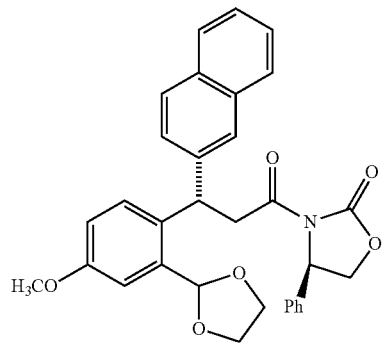 [SMILES: COc1ccc([C@@H](CC(=O)N2C(=O)OC[C@H]2c2ccccc2)c2ccc3ccccc3c2)c(C2OCCO2)c1]

To a solution of copper(I) bromide-dimethyl sulfide complex (1.43 g, 6.9 mmol) in anhydrous THF (33 mL) and dimethyl sulfide (16.5 mL) at −78° C. was added 2-naphthylene magnesium bromide (27.3 mL, 0.5 M in THF) slowly via syringe. After the addition, the reaction solution was stirred at −40° C. for 30 min, and then re-cooled to −78° C. A solution of Compound 21 (1.8 g, 4.6 mmol) in THF (24 mL) was then added via syringe. The reaction mixture was slowly warmed to room temperature before it was quenched with aqueous ammonium chloride at 0° C. and extracted with ethyl acetate (2×). The combined organic extract was washed with 1:1 water/brine, dried over sodium sulfate and concentrated in vacuo. The residue obtained was purified by flash column chromatography (hexanes/ethyl acetate 95:5 to 55:45) to give compound 22 (2.15 g, 85%) as an off-white foam: $^1$H NMR (CDCl$_3$, 500 MHz) 7.72-7.70 (m, 2H), 7.69-7.63 (m, 2H), 7.46-7.40 (m, 2H), 7.37 (d, J=8.5 Hz, 1H), 7.24 (d, J=8.5 Hz, 1H), 7.17-7.11 (m, 2H), 7.04 (t, J=7.5 Hz, 2H), 6.99 (d, J=7.5 Hz, 2H), 6.81 (s, J=8.5 Hz, 1H), 6.09 (s, 1H), 5.34-5.30 (m, 2H), 4.59 (t, J=8.5 Hz, 1H), 4.16-4.14 (m, 3H), 4.06-4.01 (m, 3H), 3.79 (s, 3H), 3.60 (dd, J=16.5, 8.5 Hz, 1H).

Preparation of (S)-3-(2-(1,3-dioxolan-2-yl)-4-methoxyphenyl)-3-(naphthalen-2-yl)propanoic acid (Compound 23)

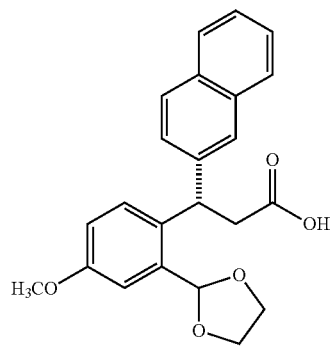 [SMILES: COc1ccc([C@@H](CC(=O)O)c2ccc3ccccc3c2)c(C2OCCO2)c1]

To a solution of compound 22 (0.55 g, 1.0 mmol) in a mixture of THF (12 mL) and water (4 mL) at 0° C. was added hydrogen peroxide (0.41 mL, 30% in water), followed by lithium hydroxide (48 mg, 2.0 mmol) in water (2.5 mL). The reaction solution was stirred at 0° C. for 1 h and room temperature for 30 min. A solution of sodium sulfite (0.78 g) in water (5 mL) was then added. After stirring at 0° C. for 10 min, the mixture was concentrated in vacuo to remove the organic solvent. The remaining aqueous solution was diluted with aqueous sodium hydroxide and extracted with dichloromethane. The basic aqueous layer was separated, neutralized with aqueous ammonium chloride to pH 6-7 and then extracted with dichloromethane (3×). The combined organic extract was dried over sodium sulfate and concentrated in vacuo to give compound 23 (0.41 g, crude), which was used in the next step without further purification: $^1$H NMR (500 MHz, CDCl$_3$) δ 7.56-7.70 (m, 4H), 7.48-7.33 (m, 3H), 7.13 (d, J=2.5 Hz, 1H), 7.08 (d, J=8.5 Hz, 1H), 6.80 (dd, J=9.0, 3.0 Hz, 1H), 6.08 (s, 1H), 5.18 (dd, J=9.0, 7.0 Hz, 1H), 4.21-4.00 (m, 4H), 3.77 (s, 3H), 3.20 (dd, J=16.0, 9.0 Hz, 1H), 3.12 (dd, J=16.0, 7.0 Hz, 1H).

Preparation of (S)-methyl 2-(2-(1,3-dioxolan-2-yl)-4-methoxyphenyl)-2-(naphthalen-2-yl)ethylcarbamate (Compound 24)

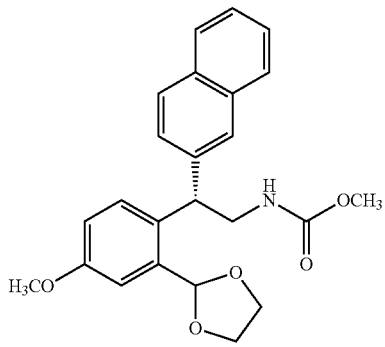 [SMILES: COC(=O)NC[C@@H](c1ccc2ccccc2c1)c1ccc(OC)cc1C1OCCO1]

To a solution of compound 23 (0.38 g, 1.0 mmol) and triethylamine (0.15 mL, 1.0 mmol) in toluene (10 mL) at 85-90° C. was added diphenylphosphorylazide (0.21 mL, 1.0 mmol) via syringe. The reaction mixture was stirred for 30 min, then it was cooled to 50° C. and methanol (0.30 mL, 7.5 mmol) was added to it. The resultant solution was stirred at 50° C. for 14 h, then cooled to room temperature, diluted with ethyl acetate and washed with aqueous ammonium chloride. The organic extract was dried over sodium sulfate and concentrated in vacuo. Purification by flash column chromatography (hexanes/ethyl acetate 95:5 to 50:50) gave compound 24 (0.24 g, 59%) as a white foam: $^1$H NMR (500 MHz, CDCl$_3$) 7.81-7.72 (m, 4H), 7.48-7.42 (m, 2H), 7.33 (d, J=8.5 Hz, 1H), 7.17-7.14 (m, 2H), 6.84 (dd, J=8.5, 2.5 Hz, 1H), 6.05 (s, 1H), 5.22 (br s, 1H), 4.81 (t, J=8.0 Hz, 1H), 4.22-4.07 (m, 4H), 3.98-3.87 (m, 2H), 3.79 (s, 3H), 3.71-3.52 (m, 3H).

Preparation of (S)-methyl 7-methoxy-4-(naphthalen-2-yl)-3,4-dihydroisoquinoline-2(1H)-carboxylate (Compound 25)

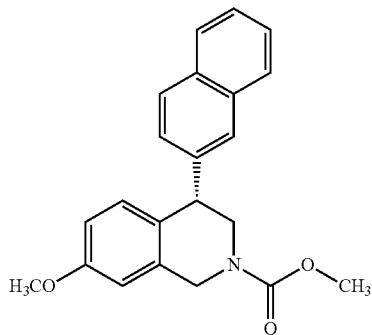 [SMILES: COC(=O)N1Cc2cc(OC)ccc2[C@H](c2ccc3ccccc3c2)C1]

To a solution of compound 24 (0.10 g, 0.25 mmol) in 1,4-dioxane (10 mL) at 0° C. was added concentrated HCl (0.8 mL). The reaction solution was stirred at room temperature for 20 min, and then quenched with aqueous sodium bicarbonate and extracted with dichloromethane (2×). The combined organic extract was dried over sodium sulfate and concentrated in vacuo. The residue obtained was dissolved in a mixture of ethanol (30 mL) and trifluoroacetic acid (2 mL). Palladium on carbon (105 mg) was added and the reaction mixture was shaken under hydrogen (25 psi) for 15 min, then filtered through a pad of CELITE® and concentrated in vacuo. The residue was dissolved in dichloromethane and the resulting solution was washed with aqueous sodium bicarbonate, dried over sodium sulfate and concentrated in vacuo. Purification by preparative thin layer chromatography (hexanes/ethyl acetate 75:25) provided compound 25 (52 mg, 60%) as a colorless oil: $^1$H NMR (500 MHz, CDCl$_3$) 7.82-7.74 (m, 3H), 7.62-7.51 (m, 1H), 7.47-7.44 (m, 2H), 7.24 (d, J=9.0 Hz, 1H), 6.85 (d, J=8.5 Hz, 1H), 6.80-6.68 (m, 2H), 4.83-4.60 (m, 2H), 4.40-3.90 (m, 2H), 3.81 (s, 3H), 3.76-3.42 (m, 4H); ESI MS m/z 348 [M+H]$^+$.

Preparation of (S)-7-methoxy-2-methyl-4-(naphthalen-2-yl)-1,2,3,4-tetrahydroisoquinoline (Compound 7)

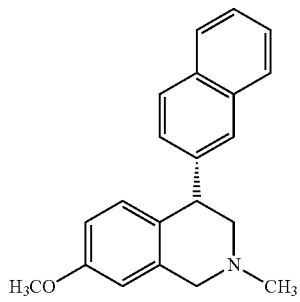

To a solution of compound 25 (51 mg, 0.15 mmol) in THF (8 mL) at 0° C. was added lithium aluminum hydride (0.6 mL, 1 M in THF) dropwise. After the addition, the reaction solution was heated under reflux for 1 h, cooled to 0° C. and quenched by sequential addition of water (1.8 mL), aqueous sodium hydroxide (0.6 mL) and water (0.6 mL). The resultant mixture was stirred at 0° C. for 10 min before it was filtered. The filtrate was extracted with dichloromethane (2×). The combined organic extract was dried over sodium sulfate and concentrated in vacuo. Purification by preparative thin layer chromatography (dichloromethane/methanol/concentrated ammonia 95:4.5:0.5) provided compound 7 (32.0 mg, 70%, AUC HPLC 96.8%, CHIRALPAK® AD 100%) as a light yellow oil: $[\alpha]^{23}_D$ +50.7° (c 0.18, methanol); $^1$H NMR (500 MHz, CDCl$_3$) 7.79-7.68 (m, 3H), 7.68 (s, 1H), 7.47-7.43 (m, 2H), 7.28-7.26 (m, 1H), 6.80 (d, J=8.0 Hz, 1H), 6.65-6.62 (m, 2H), 4.39 (dd, J=8.5, 6.0 Hz, 1H), 3.78 (s, 3H), 3.77 (d, J=15.0 Hz, 1H), 3.65 (d, J=14.5 Hz, 1H), 3.09 (dd, J=11.5, 5.5 Hz, 1H), 2.64 (dd, J=11.5, 9.0 Hz, 1H), 2.44 (s, 3H); ESI MS m/z 304 [M+H]$^+$. This compound co-elutes with authentic compound 7 on CHIRALPAK® AD (90:10:0.1 heptane:IPA:diethyl amine, I mL/min, RT=14.3 min. The RT of the (−)-enantiomer of compound 7=6.2 min).

Preparation of 1-(3-bromophenyl)-N-methylmethanamine (Compound 14)

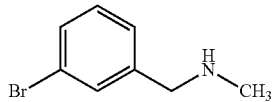

To a solution of 3-bromobenzaldehyde (138 g, 0.74 mol) in methanol (0.9 L) was added a 40% aqueous solution of methylamine (64 mL, 0.82 mol) followed by stirring at 0° C. for 1 h. Sodium borohydride (42.3 g, 1.1 mol) was added in portions at 0° C. and the reaction mixture was stirred overnight while warming to room temperature. The solution was concentrated, then diluted with water (300 mL). The resulting solution was extracted with methylene chloride (3×300 mL) and chloroform (2×300 mL). The combined organic extracts were washed with brine (2×200 mL) then dried over sodium sulfate, filtered and concentrated under reduced pressure to afford crude compound 14 (148 g) as a clear oil, which was used in the next step without further purification: $^1$H NMR (CDCl$_3$, 300 MHz) 0.7.48 (s, 1H), 7.39-7.34 (m, 1H), 7.27-7.16 (m, 2H), 3.71 (s, 2H), 2.43 (s, 3H), 1.38 (s, 1H).

Preparation of 2-((3-bromobenzyl)(methyl)amino)-1-(naphthalen-2-yl)ethanone (Compound 15)

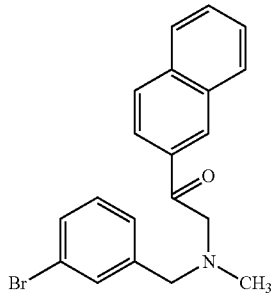 [SMILES: CN(CC(=O)c1ccc2ccccc2c1)Cc1cccc(Br)c1]

To a solution of compound 14 (23.1 g, 115.5 mmol) in methylene chloride (500 mL) was added α-bromo-2'-acetonapthone (27.9 g, 110.0 mmol) and the resulting mixture was stirred at 0° C. for 1 h prior to the addition of triethylamine (15.3 mL, 47.4 mmol). The reaction mixture was stirred at 0° C. for 2 h. The resulting mixture was diluted with water (200 mL) and the aqueous phase was extracted with additional methylene chloride (2×200 mL). The combined extracts were dried over sodium sulfate, filtered and concentrated to afford compound 15 (44.5 g) as a light yellow oil, which was used in the next step without further purification: $^1$H NMR (CDCl$_3$, 500 MHz) 8.49 (s, 1H), 8.01 (dd, J=8.8, 1.8 Hz, 1H), 7.95 (d, J=8.0 Hz, 1H), 7.90-7.84 (m, 2H), 7.62-7.52 (m, 3H), 7.40 (d, J=8.0 Hz, 1H), 7.31 (d, J=8.0 Hz, 1H), 7.19 (t, J=7.7 Hz, 1H), 3.91 (s, 2H), 3.68 (s, 2H), 2.40 (s, 3H).

Preparation of 2-((3-bromobenzyl)(methyl)amino)-1-(naphthalen-2-yl)ethanol (Compound 16)

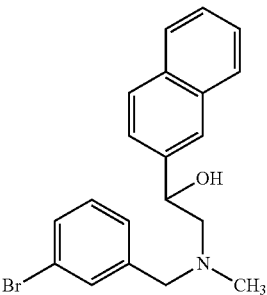 [SMILES: CN(Cc1cccc(Br)c1)CC(O)c1ccc2ccccc2c1]

To a solution of compound 15 (~110 mmol) in methanol (600 mL), sodium borohydride (5.4 g, 142.8 mmol) was added in portions at 0° C. The reaction mixture was first stirred overnight while warming up to room temperature. The reaction mixture was concentrated under reduced pressure. The residue was diluted with water (200 mL) and the solution was extracted with methylene chloride (3×300 mL). The combined organic extracts were dried over sodium sulfate, filtered and concentrated to dryness under reduced pressure to afford the crude desired product compound 16 (42.6 g) as a yellow oil, which was used without further purification in the next step: $^1$H NMR (300 MHz, CDCl$_3$) δ 7.86-7.79 (m, 4H), 7.52-7.38 (m, 5H), 7.28-7.15 (m, 2H), 4.93 (dd, J=9.5, 4.4 Hz, 1H), 4.05 (s, 1H), 3.71 (d, J=13.3 Hz, 1H), 3.52 (d, J=13.3 Hz, 1H), 2.72-2.61 (m, 2H), 2.34 (s, 3H).

Preparation of 7-bromo-2-methyl-4-(naphthalen-2-yl)-1,2,3,4-tetrahydroisoquinoline (Compound 17)

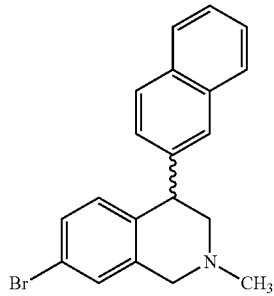 [SMILES: CN1Cc2cc(Br)ccc2C(c2ccc3ccccc3c2)C1]

To a solution of compound 16 (~110 mmol) in methylene chloride (1.0 L) was added concentrated sulfuric acid (30.0 mL, 0.56 mol) and the mixture was stirred at 0° C. for 3 h. The reaction was quenched by adding 6 N NaOH until the pH was ~9, and the aqueous phase was extracted with additional methylene chloride (3×). The combined organic extracts were dried over sodium sulfate, filtered and concentrated. The residue was purified by flash chromatography (9:1 to 8:1 hexanes/ethyl acetate) to afford compound 17 (15.79 g, 41% over 3 steps) as a white solid: $^1$H NMR (500 MHz, CDCl$_3$) 7.82-7.70 (m, 3H), 7.66 (s, 1H), 7.49-7.41 (m, 2H), 7.28-7.20 (m, 2H), 7.16 (dd, J=8.3, 2.3 Hz, 1H), 6.75 (d, J=8.5 Hz, 1H), 4.37 (dd, J=7.5, 6.5 Hz, 1H), 3.75 (d, J=15.3 Hz, 1H), 3.62 (d, J=15.3 Hz, 1H), 3.08 (ddd, J=11.5, 6.0, 1.0 Hz, 1H), 2.64 (dd, J=11.5, 8.5 Hz, 1H), 2.43 (s, 3H). The undesired 5-bromo isomer was also obtained (11.91 g, 30% over 3 steps).

Preparation of 2-methyl-4-(naphthalen-2-yl)-7-(4,4,5,5-tetramethyl-1,3,2-dioxaborolan-2-yl)-1,2,3,4-tetrahydroisoquinoline (Compound 18)

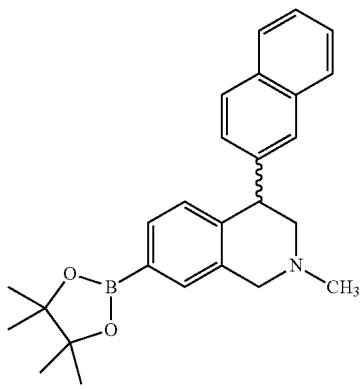 [SMILES: CN1Cc2cc(B3OC(C)(C)C(C)(C)O3)ccc2C(c2ccc3ccccc3c2)C1]

To a mixture of compound 17 (19.3 mmol), bis(pinacolato)diboron (5.9 g, 23.2 mmol), and potassium acetate (5.7 g, 57.9 mmol) was added DMSO (140 mL). The resultant solution was purged with argon for 10 min, and then dichloro[1,1'-bis(diphenylphosphino)ferrocene]palladium (II) dichloromethane adduct (1.3 g, 1.5 mmol) was added. The reaction solution was degassed again with argon for 5 min, then heated at 80° C. (oil bath) for 1 h. The resultant solution was cooled to room temperature, diluted with ethyl acetate and washed with water and brine. The organic layer was separated, dried over sodium sulfate and concentrated under reduced pressure. The crude boronate ester 2-methyl-4-(naphthalen-2-yl)-7-(4,4,5,5-tetramethyl-1,3,2-dioxaborolan-2-yl)-1,2,3,4-tetrahydroisoquinoline compound 18 (10.0 g), obtained as a brown foam, was used in the next step without further purification: ESI MS m/z 400 [M+H]$^+$.

Preparation of rac-6-(2-methyl-4-(naphthalen-2-yl)-1,2,3,4-tetrahydroisoquinolin-7-yl)pyridazin-3-amine (rac-1)

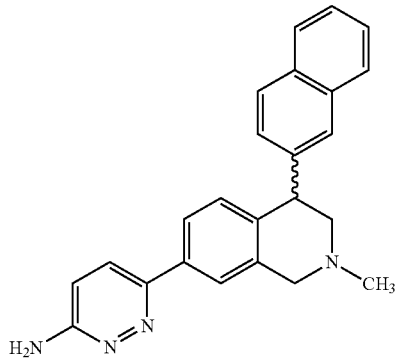

To a mixture of compound 18 (6.0 g, 15.0 mmol), 3-amino-6-chloropyridazine (3.0 g, 22.5 mmol) and cesium carbonate (14.7 g, 45.0 mmol) were added DMF (140 mL) and water (35 mL). The reaction solution was flushed with argon for 10 min, and then dichloro[1,1'-bis(diphenylphosphino)ferrocene]palladium(II) dichloromethane adduct (1.2 g, 1.5 mmol) was added. The resultant mixture was flushed with argon for 5 min and heated at 80° C. for 1 h. The reaction solution was then cooled to room temperature, diluted with ethyl acetate, washed with 1:1 brine and water (2×), dried over sodium sulfate and concentrated in vacuo. The crude product was purified by flash column chromatography (92:2:5.4:0.6 to 47:47:5.4:0.6 dichloromethane/ethyl acetate/methanol/concentrated ammonium hydroxide) to give rac-1 (3.2 g, 58%) as a light tan solid: $^1$H NMR (500 MHz, CDCl$_3$) 7.82-7.76 (m, 4H), 7.71 (s, 1H), 7.61-7.57 (m, 2H), 7.47-7.43 (m, 2H), 7.30 (dd, J=8.0, 1.5 Hz, 1H), 6.99 (d, J=8.0 Hz, 1H), 6.80 (d, J=9.5 Hz, 1H), 4.71 (br s, 2H), 4.50 (t, J=7.0 Hz, 1H), 3.89 (d, J=15.0 Hz, 1H), 3.74 (d, J=14.5 Hz, 1H), 3.14 (dd, J=11.5, 6.0 Hz, 1H), 2.70 (dd, J=11.5, 9.0 Hz, 1H), 2.48 (s, 3H); ESI MS m/z 367 [M+H]$^+$.

Preparation of (S)-6-(2-methyl-4-(naphthalen-2-yl)-1,2,3,4-tetrahydroisoquinolin-7-yl)pyridazin-3-amine (Compound 2)

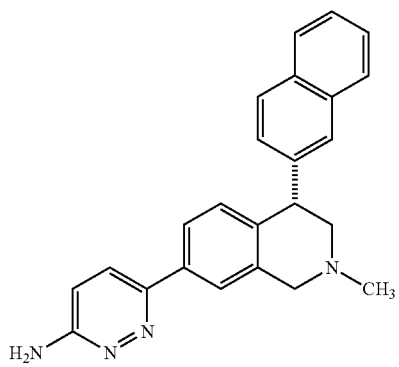 [SMILES: CN1Cc2cc(-c3ccc(N)nn3)ccc2[C@H](c2ccc3ccccc3c2)C1]

Rac-1 (3.3 g) was resolved by preparative chiral HPLC (CHIRALCEL® OD column, using 80:20:0.1 heptane/ethanol/diethylamine as the eluent) to give the (S)-enantiomer compound 2 [[α]$^{25}_D$ +122.0° (c 0.15, methanol)] (1.6 g) as a light brown foam and the (R)-enantiomer [[α]$^{25}_D$ −124.3° (c 0.23, methanol)] (1.6 g) as an off-white solid.

Preparation of (S)-6-(2-methyl-4-(naphthalen-2-yl)-1,2,3,4-tetrahydroisoquinolin-7-yl)pyridazin-3-amine, L-tartrate (Compound 2, L-tartrate)

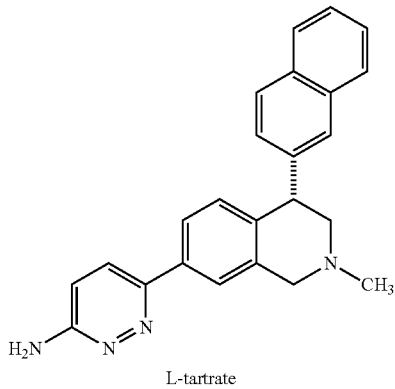 [SMILES: CN1Cc2cc(-c3ccc(N)nn3)ccc2[C@H](c2ccc3ccccc3c2)C1]

L-tartrate

To a mixture of compound 2, free base (1.6 g, 4.3 mmol) and L-tartaric acid (0.65 g, 4.3 mmol) were added methanol (280 mL) and water (100 mL). The reaction slurry was sonicated and heated at approximately 55° C. to give a clear solution, which was then concentrated in vacuo to about 100 mL. The resulting solution was lyophilized to give compound 2-L-tartrate (2.18 g, 98.6%, AUC HPLC>99%) as an off-white solid: mp 153-158° C.; $^1$H NMR (500 MHz, CDCl$_3$) 7.87-7.80 (m, 6H), 7.69 (dd, J=8.0, 1.5 Hz, 1H), 7.51-7.48 (m, 2H), 7.30 (dd, J=8.5, 1.5 Hz, 1H), 7.04-7.01 (m, 2H), 4.71 (dd, J=11.0, 5.5 Hz, 1H), 4.43 (s, 2H), 4.39 (d, J=16.0 Hz, 1H), 4.29 (d, J=15.5 Hz, 1H), 3.64 (dd, J=11.5, 5.5 Hz, 1H), 3.37-3.30 (m, 1H), 2.85 (s, 3H); ESI MS m/z 367 [M+H]$^+$; Anal. Calcd. For C$_{24}$H$_{22}$N$_4$·C$_4$H$_6$O$_6$·H$_2$O: C, 62.91; H, 5.66; N, 10.48. Found: C, 62.81; H, 5.73; N, 10.30.

Preparation of (S)-6-(2-methyl-4-(naphthalen-2-yl)-1,2,3,4-tetrahydroisoquinolin-7-yl)pyridazin-3-amine, L-tartrate (Compound 2, L-tartrate salt)

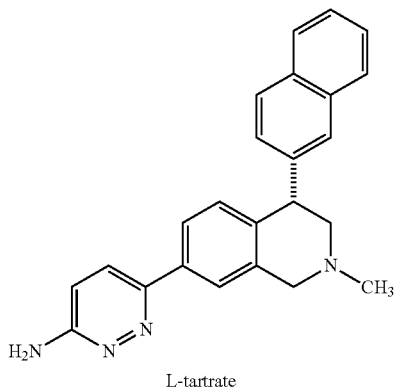 [SMILES: CN1Cc2cc(-c3ccc(N)nn3)ccc2[C@H](c2ccc3ccccc3c2)C1]

L-tartrate

Alternative procedure: To a slurry of compound 2, free base (1.5 g, 4.1 mmol) in methanol (80 mL) was added a solution of L-tartaric acid (0.63 g, 4.2 mmol) in methanol (15 mL) and water (10 mL). The reaction slurry became a clear solution after heating under reflux. The resulting solution was then cooled to 0° C. while stirring and precipitation occurred. The precipitate obtained was collected by filtration. This solid was re-crystallized twice from methanol (150 mL) and water (20 mL). The resulting solid was dissolved in methanol (25 mL) and water (100 mL), and the solution was lyophilized to give the L-tartrate salt of compound 2, (1.4 g, 65%, AUC HPLC>99%) as a white solid: [α]$^{23}_D$ +79.1° (c 0.15, methanol); $^1$H NMR (500 MHz, CDCl$_3$) 7.87-7.80 (m, 6H), 7.69 (dd, J=8.0, 1.5 Hz, 1H), 7.51-7.48 (m, 2H), 7.30 (dd, J=8.5, 1.5 Hz, 1H), 7.04-7.01 (m, 2H), 4.71 (dd, J=11.0, 5.5 Hz, 1H), 4.43 (s, 2H), 4.39 (d, J=16.0 Hz, 1H), 4.29 (d, J=15.5 Hz, 1H), 3.64 (dd, J=11.5, 5.5 Hz, 1H), 3.37-3.30 (m, 1H), 2.85 (s, 3H); ESI MS m/z 367 [M+H]$^+$.

Form N-1 was analyzed using one or more of the testing methods described below.

Single Crystal X-Ray Measurements

A Nonius Kappa CCD diffractometer equipped with graphite-monochromated Mo Kα radiation (λ=0.7107 Å) was used to collect diffraction data at the room temperature (Nonius 2001a. Data Collection Software for Nonius Kappa-CCD devices. Nonius BV, Delft, The Netherlands. Nonius 2001b; DENZO Processing Software for Nonius Kappa-CCD devices, Nonius BV, Delft, The Netherlands). The final unit cell parameters were determined using the entire data set.

All structures were solved by direct methods and refined by the full-matrix least-squares techniques, using the SHELXTL software package (Sheldrick, G. M. (1997), SHELXTL. Structure Determination Programs. Version 5.10, Bruker AXS, Madison, Wis., USA.). The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)_2/\Sigma_w|F_o|^2]^{1/2}$, where w is an appropriate weighting function based on errors in the observed intensities. Difference Fourier maps were examined at all stages of refinement. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

The crystal data of the N-1 form is shown in Table 2. The fractional atomic coordinates are listed in Table 3. It should be understood by one of ordinary skill in the art that slight variations in the coordinates are possible and are considered to be within the scope the present disclosure.

TABLE 2

| Crystal Data of Form N-1 | |
|---|---|
| Temperature | room temperature |
| Wavelength | 0.71073 Å |
| Crystal system, space group | Monoclinic, P2$_1$ |
| Unit cell dimensions | a = 8.4299(4) Å alpha = 90° |
| | b = 6.0698(3) Å beta = 100.169(2)° |
| | c = 19.0689(12) Å gamma = 90° |
| Volume | 960.39(9) Å$^3$ |
| Z, Calculated density | 2, 1.267 g/cm$^3$ |

TABLE 3

Atomic Coordinates

| | x | y | z | U(eq) |
|---|---|---|---|---|
| N1 | 0.3248(4) | −0.7759(7) | −0.0061(2) | 0.0608(10) |
| N2 | 0.3353(4) | −0.4151(6) | 0.0322(2) | 0.0516(9) |
| N3 | 0.2832(4) | −0.2519(6) | 0.07049(19) | 0.0504(8) |
| N4 | −0.2362(4) | 0.4479(6) | 0.20586(19) | 0.0525(9) |
| C1 | 0.2608(5) | −0.6106(7) | 0.0275(2) | 0.0476(9) |
| C2 | 0.1165(5) | −0.6421(7) | 0.0547(2) | 0.0476(9) |
| C3 | 0.0665(5) | −0.4763(7) | 0.0935(2) | 0.0487(9) |
| C4 | 0.1596(4) | −0.2835(6) | 0.1041(2) | 0.0439(8) |
| C5 | 0.1240(5) | −0.1073(6) | 0.1527(2) | 0.0453(9) |
| C6 | −0.0334(4) | −0.0444(6) | 0.1549(2) | 0.0447(9) |
| C7 | −0.0674(4) | 0.1306(6) | 0.1973(2) | 0.0446(9) |
| C8 | −0.2368(5) | 0.2120(8) | 0.1916(3) | 0.0556(10) |
| C9 | −0.3995(6) | 0.5360(11) | 0.1966(4) | 0.0778(15) |
| C10 | −0.1522(5) | 0.4871(7) | 0.2779(2) | 0.0541(10) |
| C11 | 0.0289(4) | 0.4359(6) | 0.2862(2) | 0.0463(9) |
| C12 | 0.0594(4) | 0.2382(7) | 0.2416(2) | 0.0441(8) |
| C13 | 0.2163(5) | 0.1695(7) | 0.2403(2) | 0.0541(11) |
| C14 | 0.2491(5) | 0.0035(8) | 0.1957(2) | 0.0528(11) |
| C15 | 0.1013(4) | 0.4074(6) | 0.3638(2) | 0.0439(8) |
| C16 | 0.1983(5) | 0.5661(6) | 0.4007(2) | 0.0445(9) |
| C17 | 0.2648(4) | 0.5393(6) | 0.4738(2) | 0.0450(9) |
| C18 | 0.3664(5) | 0.6998(7) | 0.5124(2) | 0.0533(10) |
| C19 | 0.4321(6) | 0.6659(9) | 0.5822(3) | 0.0681(13) |
| C20 | 0.4004(6) | 0.4740(9) | 0.6174(2) | 0.0661(13) |
| C21 | 0.3015(5) | 0.3166(8) | 0.5816(3) | 0.0611(11) |
| C22 | 0.2296(4) | 0.3441(7) | 0.5095(2) | 0.0449(9) |
| C23 | 0.1271(5) | 0.1861(7) | 0.4707(2) | 0.0529(10) |
| C24 | 0.0654(5) | 0.2157(7) | 0.4011(2) | 0.0527(10) |
| H1A | 0.4107 | −0.7535 | −0.0236 | 0.073 |
| H1B | 0.2796 | −0.9034 | −0.0099 | 0.073 |
| H16 | 0.2208 | 0.6937 | 0.3773 | 0.053 |
| H11 | 0.0810 | 0.5636 | 0.2684 | 0.056 |
| H6 | −0.1181 | −0.1205 | 0.1275 | 0.054 |
| H14 | 0.3554 | −0.0346 | 0.1945 | 0.063 |
| H24 | −0.0020 | 0.1086 | 0.3769 | 0.063 |
| H3 | −0.0272 | −0.4903 | 0.1126 | 0.058 |
| H13 | 0.3012 | 0.2375 | 0.2703 | 0.065 |
| H19 | 0.4991 | 0.7727 | 0.6068 | 0.082 |
| H2 | 0.0579 | −0.7721 | 0.0463 | 0.057 |
| H21 | 0.2812 | 0.1886 | 0.6054 | 0.073 |
| H20 | 0.4462 | 0.4531 | 0.6650 | 0.079 |
| H10A | −0.1992 | 0.3957 | 0.3106 | 0.065 |
| H10B | −0.1662 | 0.6399 | 0.2904 | 0.065 |
| H23 | 0.1014 | 0.0591 | 0.4936 | 0.063 |
| H8A | −0.2964 | 0.1828 | 0.1442 | 0.067 |
| H8B | −0.2897 | 0.1348 | 0.2257 | 0.067 |
| H18 | 0.3887 | 0.8294 | 0.4900 | 0.064 |
| H9A | −0.4538 | 0.4762 | 0.2325 | 0.117 |
| H9B | −0.4572 | 0.4962 | 0.1503 | 0.117 |
| H9C | −0.3952 | 0.6936 | 0.2008 | 0.117 |

Powder X-Ray Diffraction

X-ray powder diffraction (PXRD) data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were collected for $3 \leq 2\theta \leq 35°$ with a sample exposure time of at least 1000 seconds. The resulting two-dimensional diffraction arcs were integrated to create a traditional 1-dimensional PXRD.

The results of the PXRD pattern and a simulated pattern calculated from the single crystal data are shown in FIG. 1.

Table 4 lists the characteristic PXRD peaks that describe Form N-1 of Compound 2.

TABLE 4

Characteristic diffraction peak positions (degrees 2θ ± 0.1) at room temperature, based on a high quality pattern collected with a diffractometer (cuKα) with a spinning capillary with 2θ calibrated with a NIST other suitable standard

N-1

4.6
9.4
10.6
14.1
15.4
18.2
19.5

Differential Scanning calorimetry

Differential scanning calorimetry (DSC) experiments were performed in a TA INSTRUMENTS® model Q1000 or 2920. The sample (about 2-6 mg) was weighed in a pin-pricked hermetically sealed aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Figure 2:
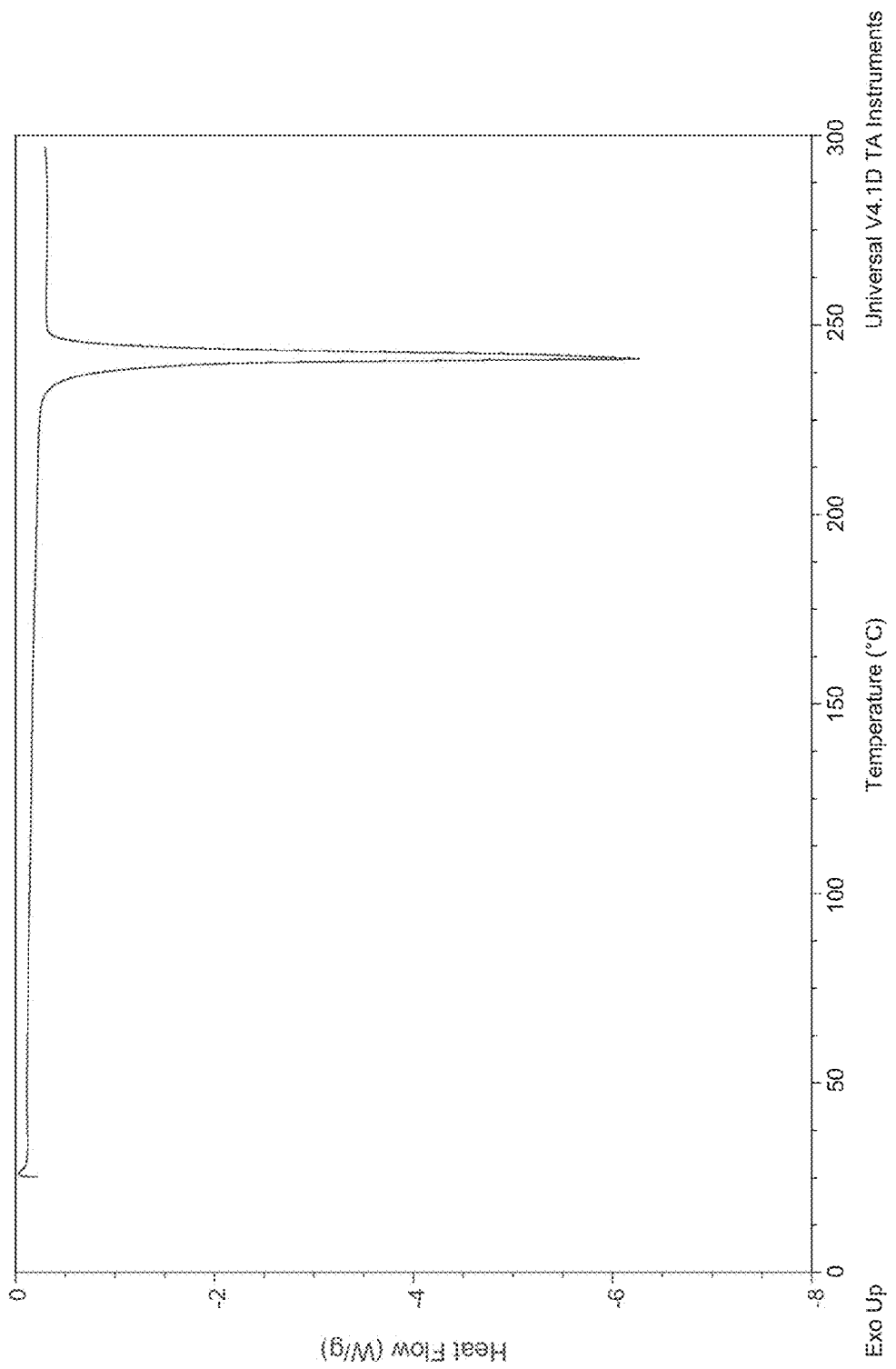
FIG. 2 illustrates the differential scanning calorimetry pattern of Form N-1.

The results are shown in FIG. 2.

Solid-State Nuclear Magnetic Resonance (SSNMR)

All solid-state C-13 NMR measurements were made with a Bruker DSX-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (Bennett, A. E. et al., *J. Chem. Phys.*, 103:6951 (1995); Metz, G. et al., *J. Magn. Reson. A*, 110:219-227 (1994)). Approximately 70 mg of sample, packed into a canister-design zirconia rotor was used for each experiment. Chemical shifts (5) were referenced to external adamantane with the high frequency resonance being set to 38.56 ppm (Earl, W. L. et al., *J. Magn. Reson.*, 48:35-54 (1982)).

Figure 3:
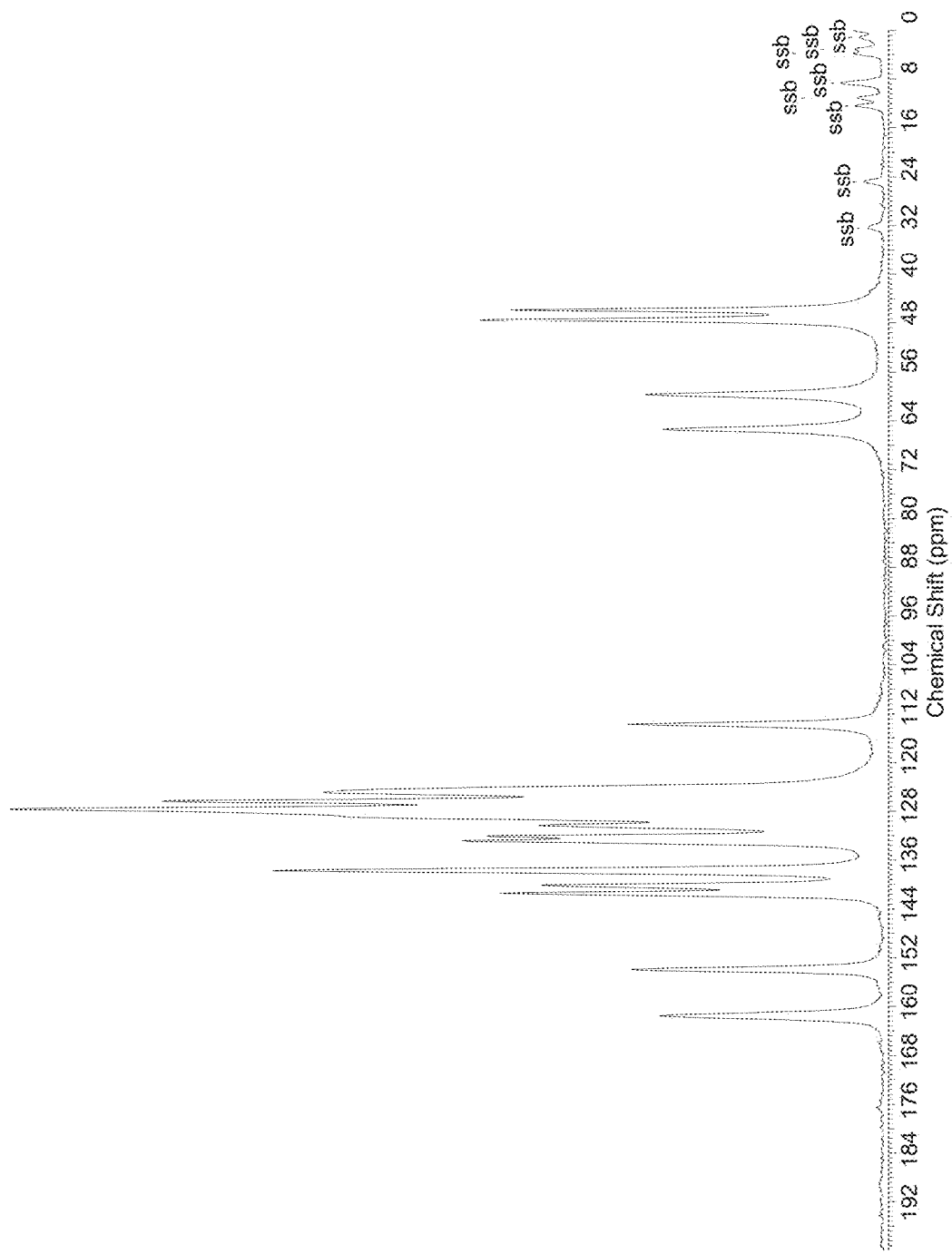
FIG. 3 illustrates the Solid State Nuclear Magnetic Resonance (SSNMR) spectrum of Form N-1.

The results are shown in FIG. 3.

In a preferred aspect, Form N-1 has the properties set for the in Table 5, below.

TABLE 5

Physical and Chemical Properties

Chemical name: 6-[(4S)-1,2,3,4-tetrahydro-2-methyl-4-(2-naphthalenyl)-7-isoquinolinyl]-3-pyridazinamine Chemical structure

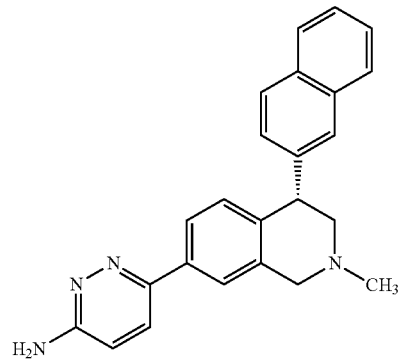 [SMILES: CN1Cc2cc(-c3ccc(N)nn3)ccc2[C@H](c2ccc3ccccc3c2)C1]

TABLE 5-continued

Physical and Chemical Properties

| | |
|---|---|
| Molecular formula | $C_{24}H_{22}N_4$ |
| Molecular weight | 366.46 |
| Appearance | White to off-white powder |
| Melting point/range | 237°-243° C. |
| Solution pH | ~7.0 at about 1 µg/mL concentration in water |
| pH-Solubility profile | At solution pH 6.5 and above, the aqueous solubility of Compound 2 is ~1 µg or less. Aqueous solubility increases at lower pH values (15.6 mg/mL at pH 2.0 and 1.76 mg/mL at pH 4.4) |
| Solubility profile (USP definition) | practically insoluble: n-heptane<br>very slightly soluble: acetonitrile, ethyl acetate, n-butanol<br>slightly soluble: isopropanol, acetone, ethanol, methanol, propylene glycol, dichloromethane<br>sparingly soluble: PEG 400<br>soluble: N,N-dimethylacetamide, dimethylsulfoxide<br>freely soluble: tetrahydrofuran |
| $pK_a$ | 4.9 and 7.8 |
| Distribution coefficient | Log $D_{o/b}$ = 3.10 at pH 6.5 and 3.82 at pH 7.4 |
| Stability | Compound 2 is stable up to 25° C. with protection from light. |

The examples and characterizations provided above are not intended to limit the scope of the invention. For example, Form N-1 may be useful in the form of the free base or acid or in the form of a pharmaceutically acceptable salt thereof. Similarly, it may be desirable to utilize a prodrug of form N-1.

What is claimed is:

1. A method of treating depression in a mammal in need thereof comprising administering to the mammal a therapeutically-effective amount of Form N-1 of

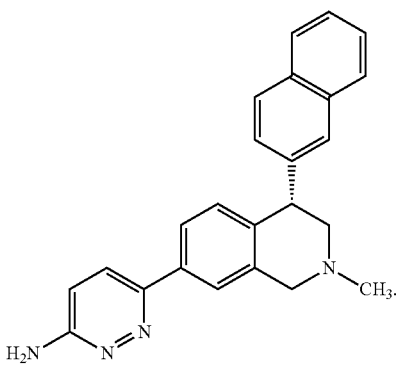 [SMILES: CN1Cc2cc(-c3ccc(N)nn3)ccc2[C@H](c2ccc3ccccc3c2)C1]

2. The method of claim 1 wherein the mammal is a human.

* * * * *